US009757074B2

(12) United States Patent
    Dawson

(10) Patent No.: US 9,757,074 B2
(45) Date of Patent: *Sep. 12, 2017

(54) NON-RESISTIVE CONTACT ELECTRICAL SYSTEMS AND METHODS FOR VISUALIZING THE STRUCTURE AND FUNCTION OF OBJECTS OR SYSTEMS

(71) Applicant: RESCON LTD, Farnborough (GB)

(72) Inventor: Thomas Andrew Dawson, Aldershot (GB)

(73) Assignee: RESCON LTD, Cronall (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/279,683

(22) Filed: Sep. 29, 2016

(65) Prior Publication Data

US 2017/0014088 A1    Jan. 19, 2017

Related U.S. Application Data

(63) Continuation of application No. 14/740,099, filed on Jun. 15, 2015, now Pat. No. 9,456,758, which is a
(Continued)

(51) Int. Cl.

| A61B 5/00 | (2006.01) |
|---|---|
| A61B 5/0492 | (2006.01) |
| A61B 5/0478 | (2006.01) |
| A61B 5/0408 | (2006.01) |
| G01N 27/60 | (2006.01) |
| A61B 8/08 | (2006.01) |
| A61B 6/12 | (2006.01) |

(Continued)

(52) U.S. Cl.
    CPC ........... *A61B 5/742* (2013.01); *A61B 5/01* (2013.01); *A61B 5/04* (2013.01); *A61B 5/04001* (2013.01); *A61B 5/04002* (2013.01); *A61B 5/0408* (2013.01); *A61B 5/0478* (2013.01); *A61B 5/0492* (2013.01); *A61B 5/0536* (2013.01); *A61B 5/061* (2013.01); *A61B 5/062* (2013.01); *A61B 5/08* (2013.01); *A61B 6/12* (2013.01); *A61B 8/0841* (2013.01); *G01N 27/00* (2013.01); *G01N 27/60* (2013.01); *G01N 35/00* (2013.01); *A61B 5/04011* (2013.01); *A61B 2503/40* (2013.01)

(58) Field of Classification Search
    CPC ......... A61B 2503/40; A61B 5/01; A61B 5/04; A61B 5/04001; A61B 5/04002; A61B 5/04011; A61B 5/0408; A61B 5/0478; A61B 5/0492; A61B 5/0536; A61B 5/061; A61B 5/062; A61B 5/08; A61B 5/742; A61B 6/12; A61B 8/0841; G01N 27/00; G01N 27/60; G01N 35/00

See application file for complete search history.

(56) References Cited

U.S. PATENT DOCUMENTS

| 5,146,926 A | * | 9/1992 | Cohen | ............... G06K 9/0057 600/523 |
|---|---|---|---|---|
| 9,057,713 B2 | * | 6/2015 | Dawson | .................. A61B 5/04 |
| 9,456,758 B2 | * | 10/2016 | Dawson | .................. A61B 5/04 |

* cited by examiner

*Primary Examiner* — Michael Rozanski
(74) *Attorney, Agent, or Firm* — Tillman Wright, PLLC; Chad D. Tillman; Jeremy C. Doerre

(57) ABSTRACT

Methods and systems for sensing properties of an object or entity utilize non-resistive contact sensors alone or in combination with other sensors. The sensor data is utilized for detecting and visualizing properties of one or more biological or non-biological objects or entities.

20 Claims, 39 Drawing Sheets

Related U.S. Application Data continuation of application No. 13/775,112, filed on Feb. 22, 2013, now Pat. No. 9,057,713.

(60) Provisional application No. 61/602,050, filed on Feb. 22, 2012.

(51) Int. Cl.
*A61B 5/08* (2006.01)
*A61B 5/01* (2006.01)
*A61B 5/053* (2006.01)
*A61B 5/04* (2006.01)
*A61B 5/06* (2006.01)
*G01N 35/00* (2006.01)
*G01N 27/00* (2006.01)

smaller normal electrical problems normal changing shape normal

T(o)

< 3D MATRIX TRANSFER FUNCTION >

T(i)

< 3D MATRIX TRANSFER FUNCTION >

T(ii)

< 3D MATRIX TRANSFER FUNCTION >

NON-RESISTIVE CONTACT ELECTRICAL SYSTEMS AND METHODS FOR VISUALIZING THE STRUCTURE AND FUNCTION OF OBJECTS OR SYSTEMS

CROSS-REFERENCE TO RELATED APPLICATION

The present application is a U.S. continuation of, and claims priority under 35 U.S.C. §120 to, U.S. nonprovisional patent application Ser. No. 14/740,099, filed 2015 Jun. 15, now U.S. Pat. No. 9,456,758 which '099 application is a U.S. continuation of, and claims priority under 35 U.S.C. §120 to, U.S. nonprovisional patent application Ser. No. 13/775,112, filed Feb. 22, 2013, now U.S. Pat. No. 9,057,713 which '112 application is a nonprovisional patent application of, and claims priority under 35 U.S.C. §119(e) to, U.S. provisional patent application 61/602,050, filed Feb. 22, 2012. Each of the '112 application and '050 application is hereby incorporated herein by reference. The present application also hereby incorporates herein by reference the entire disclosure of U.S. nonprovisional patent application Ser. No. 13/527,862.

COPYRIGHT STATEMENT

All of the material in this patent document is subject to copyright protection under the copyright laws of the U.S. and other countries. The copyright owner has no objection to the facsimile reproduction by anyone of the patent document or the patent disclosure, as it appears in official governmental records. All other copyright rights whatsoever are reserved.

BACKGROUND OF THE INVENTION

Data reconstruction and visualization is increasingly being used as a method to assist in the communication and analysis of complex data sets. It has been effectively used in conveying structural and functional data with good examples being magnetic resonance imaging (MRI) and computerized tomography (CT). Such an approach, however, has not been effectively developed and utilized for representation of electrophysiological data, both alone and, in particular, in combination with other data types.

For example, many conventional systems recording physiological electrical activity rely on conductive contact and hence active draw of current, which can be disadvantageous. Such a system may employ resistive contact sensors that require electrical contact with a surface for effective transduction of the biological surface potential into an electronic format. However, due to the resistive contact the signal is drawn away from the source making signal reconstruction difficult. For example, resistive contact electrodes draw current away from a source, thus corrupting the signal, making reconstruction more technically challenging. Thus, such an approach can corrupt a measured signal, especially for other sensors in close proximity. Also, resistive contact sensors in close proximity can short out. Resistive contact sensor signals are also vulnerable to alteration in the conducting medium between the sensor and the entity being measured. A working example of this would be dilution of a silver chloride conducting gel by sweat. This can significantly limit the ability of active conducting sensors to be used as a data source for accurate reconstructions of electrical activity. Further, in emergency situations or when a surface is compromised, this approach can make it difficult to efficiently get a clear signal Notably, conventional devices considered to be the gold standard in medical diagnostic electrophysiology, the electrocardiogram (EKG), the electromyogram (EMG) and the electroencephalogram (EEG), can suffer from such disadvantages, especially when it is desirable to use non-adhesive electrodes.

Accordingly, a need exists for improvement in medical diagnostic electrophysiology. More broadly, needs exist for systems and methods for detecting properties of biological and non-biological entities. These, and other needs, are addressed by one or more aspects of the present invention.

SUMMARY OF THE INVENTION

The present invention includes many aspects and features. Moreover, while many aspects and features relate to, and are described in one or more specific contexts, the present invention is not limited to use only in such described contexts, as will become apparent from the following summaries and detailed descriptions of aspects, features, and one or more embodiments of the present invention.

For example, an exemplary aspect relates to methods by which non-resistive contact sensors are used exclusively or in combination with other sensors and the sensor data is utilized for detecting properties of one or more biological or non-biological entities.

Another aspect relates to a method comprising positioning a plurality of non-resistive contact electric field sensors at an entity, each of the plurality of non-resistive contact electric field sensors being positioned proximate a different particular generally predetermined location; repeatedly measuring, utilizing the plurality of non-resistive contact electric field sensors, an electrical potential associated with two or more sections of a structure of the entity; and generating, utilizing data obtained from the repeated measuring, a visualization of the structure of the entity, the visualization including a depiction of each of the two or more sections of the structure.

Another aspect relates to a method comprising positioning a plurality of non-resistive contact sensors at an entity, each of the plurality of non-resistive contact sensors being positioned proximate a different particular generally predetermined location; repeatedly measuring, utilizing the plurality of non-resistive contact sensors, a magnetic potential associated with two or more sections of a structure of the entity; and generating, utilizing data obtained from the repeated measuring, a visualization of the structure of the entity, the visualization including a depiction of each of the two or more sections of the structure.

Another aspect relates to a method comprising positioning a plurality of non-resistive contact electric field sensors at an entity, each of the plurality of non-resistive contact electric field sensors being positioned proximate a different particular generally predetermined location; repeatedly measuring, utilizing the plurality of non-resistive contact electric field sensors, an electrical potential associated with two or more sections of a structure of the entity; electronically comparing data obtained from the repeated measuring to data associated with typical measurements of the structure for other entities; and generating, utilizing data obtained from the repeated measuring, a visualization of the structure of the entity, the visualization including a depiction of each of the two or more sections of the structure, together with a visualization of a typical structure generated based on the data associated with typical measurements of the structure for other entities.

Another aspect relates to a method comprising positioning a plurality of non-resistive contact electric field sensors at an entity, each of the plurality of non-resistive contact electric field sensors being positioned proximate a different particular generally predetermined location; repeatedly measuring, utilizing the plurality of non-resistive contact electric field sensors, an electrical potential associated with two or more sections of a structure of the entity; and generating, utilizing data obtained from the repeated measuring, a visualization of the structure of the entity, the visualization including a depiction of each of the two or more sections of the structure, together with a visualization of a typical structure generated based on data associated with typical measurements of the structure for other entities.

Another aspect relates to a method comprising positioning a plurality of non-resistive contact electric field sensors at an entity, each of the plurality of non-resistive contact electric field sensors being positioned proximate a different particular generally predetermined location; continually measuring, utilizing the plurality of non-resistive contact electric field sensors, an electrical potential associated with two or more sections of a structure of the entity; accessing data related to past measurements, utilizing non-resistive contact electric field sensors, of the structure of the entity; and generating, utilizing data obtained from the continual measuring, a visualization of the structure of the entity, the visualization including a depiction of each of the two or more sections of the structure, together with a visualization of a typical condition of the structure generated based on the accessed data related to past measurements of the structure of the entity.

Another aspect relates to a method comprising positioning a plurality of non-resistive contact electric field sensors at a first entity, each of the plurality of non-resistive contact electric field sensors being positioned proximate a different particular location; repeatedly measuring, utilizing the plurality of non-resistive contact electric field sensors, an electrical potential associated with two or more sections of an electrically active structure of the first entity; accessing, from a database, data corresponding to measurements of an electrically active structure, which is of the same type as the electrically active structure of the first entity, for a plurality of other entities, the measurements having been taken utilizing non-resistive contact electric field sensors; electronically determining, by comparing data obtained from the repeated measuring to the accessed data, a property of the electrically active structure of the first entity; and generating, utilizing data obtained from the repeated measuring, a visualization of the electrically active structure of the first entity, the visualization including a depiction of each of the two or more sections of the an electrically active structure, together with a visualization of a "normal" electrically active structure generated based on the accessed data corresponding to measurements of electrically active structures for a plurality of other entities.

In a feature of this aspect, electronically determining, by comparing data obtained from the repeated measuring to the accessed data, a property of the structure of the first entity comprises electronically determining, by comparing data obtained from the repeated measuring to the accessed data, an atypical property of the structure of the first entity. In at least some implementations, electronically determining, by comparing data obtained from the repeated measuring to the accessed data, an atypical property of the structure of the first entity comprises electronically determining that the structure of the first entity is smaller than a "normal" structure. In at least some implementations, electronically determining, by comparing data obtained from the repeated measuring to the accessed data, an atypical property of the structure of the first entity comprises electronically determining that the structure of the first entity is larger than a "normal" structure. In at least some implementations, electronically determining, by comparing data obtained from the repeated measuring to the accessed data, an atypical property of the structure of the first entity comprises electronically determining that the structure of the first entity is damaged. In at least some implementations, electronically determining, by comparing data obtained from the repeated measuring to the accessed data, an atypical property of the structure of the first entity comprises electronically determining that one or more of the two or more sections of the structure of the first entity is damaged.

In a feature of this aspect, electronically determining, by comparing data obtained from the repeated measuring to the accessed data, a property of the structure of the first entity comprises electronically determining that voltage measurements of the structure of the first entity are lower than typical voltage measurements from the accessed data. In at least some implementations, the determination that voltage measurements of the structure of the first entity are lower than typical voltage measurements from the accessed data is utilized to ascertain that the electrically active structure of the first entity is smaller than a "normal" electrically active structure.

In a feature of this aspect, electronically determining, by comparing data obtained from the repeated measuring to the accessed data, a property of the structure of the first entity comprises electronically determining that voltage measurements of the structure of the first entity are higher than typical voltage measurements from the accessed data. In at least some implementations, the determination that voltage measurements of the structure of the first entity are lower than typical voltage measurements from the accessed data is utilized to ascertain that the electrically active structure of the first entity is larger than a "normal" electrically active structure.

In a feature of this aspect, electronically determining, by comparing data obtained from the repeated measuring to the accessed data, a property of the structure of the first entity comprises electronically determining, by comparing data obtained from the repeated measuring to the accessed data, that the electrically active structure of the first entity has an atypical shape.

In a feature of this aspect, electronically determining, by comparing data obtained from the repeated measuring to the accessed data, a property of the structure of the first entity comprises electronically determining, by comparing data obtained from the repeated measuring to the accessed data, that one or more or of the two or more sections of the electrically active structure of the first entity has an atypical shape.

In a feature of this aspect, electronically determining, by comparing data obtained from the repeated measuring to the accessed data, a property of the structure of the first entity comprises electronically determining, by comparing data obtained from the repeated measuring to the accessed data, that the electrically active structure of the first entity has a greater area of electrically active substance in one or more of the two or more sections of the electrically active structure of the first entity.

In a feature of this aspect, electronically determining, by comparing data obtained from the repeated measuring to the accessed data, a property of the structure of the first entity comprises electronically determining, by comparing data obtained from the repeated measuring to the accessed data, that the electrically active structure of the first entity has a greater volume of electrically active substance in one or more of the two or more sections of the electrically active structure of the first entity.

In a feature of this aspect, electronically determining, by comparing data obtained from the repeated measuring to the accessed data, a property of the structure of the first entity comprises electronically determining, by comparing data obtained from the repeated measuring to the accessed data, that the electrically active structure of the first entity, as compared to a "normal" electrically active structure, has a greater area of electrically active substance in one or more of the two or more sections of the electrically active structure of the first entity.

In a feature of this aspect, electronically determining, by comparing data obtained from the repeated measuring to the accessed data, a property of the structure of the first entity comprises electronically determining, by comparing data obtained from the repeated measuring to the accessed data, that the electrically active structure of the first entity, as compared to a "normal" electrically active structure, has a greater volume of electrically active substance in one or more of the two or more sections of the electrically active structure of the first entity. In at least some implementations, the electrically active substance comprises tissue.

In a feature of this aspect, repeatedly measuring, utilizing the plurality of non-resistive contact electric field sensors, an electrical potential associated with two or more sections of an electrically active structure of the first entity comprises determining three dimensional electrical vectors associated therewith.

In a feature of this aspect, the first entity comprises a living organism.

In a feature of this aspect, the first entity comprises an animal.

In a feature of this aspect, the first entity comprises a human.

In a feature of this aspect, the plurality of non-resistive contact electric field sensors comprises at least six non-resistive contact electric field sensors.

In a feature of this aspect, the plurality of non-resistive contact electric field sensors comprises at least ten non-resistive contact electric field sensors.

In a feature of this aspect, the number of non-resistive contact electric field sensors utilized is selected based on a desired resolution of spatial information.

In a feature of this aspect, the method includes selecting a number of non-resistive contact electric field sensors to utilize based on a desired resolution of spatial information.

In a feature of this aspect, in positioning a plurality of non-resistive contact electric field sensors at a first entity, each of the plurality of non-resistive contact electric field sensors is positioned proximate a different generally predetermined particular location.

In at least some implementations, positioning a plurality of non-resistive contact electric field sensors at a first entity comprises positioning each of the plurality of non-resistive contact electric field sensors at a location proximate a predetermined portion of a body of a person.

In a feature of this aspect, the method further includes a step of utilizing one or more additional sensors to inform placement of the plurality of non-resistive contact electric field sensors.

In a feature of this aspect, wherein the method further includes a step of utilizing an ultrasound probe to inform placement of the plurality of non-resistive contact electric field sensors.

In a feature of this aspect, one or more of the non-resistive contact electric field sensors is enveloped in a biocompatible sleeve.

In a feature of this aspect, one or more of the non-resistive contact electric field sensors is enveloped in a disposable biocompatible sleeve.

In a feature of this aspect, the non-resistive contact electric field sensors are arranged as an array.

In a feature of this aspect, one of the non-resistive contact electric field sensors comprises a signal transduction component.

In a feature of this aspect, the one of the non-resistive contact electric field sensors is implanted or temporarily placed within the first entity with a membrane or structure separating the signal transduction component of the from the substance of the entity.

In a feature of this aspect, the electrically active structure comprises a heart.

In a feature of this aspect, the electrically active structure comprises a brain.

In a feature of this aspect, the electrically active structure comprises an organ.

In a feature of this aspect, the first entity comprises an inanimate object.

Another aspect relates to a method comprising positioning a plurality of non-resistive contact electric field sensors at an entity, each of the plurality of non-resistive contact electric field sensors being positioned proximate a different particular generally predetermined location; repeatedly measuring, utilizing the plurality of non-resistive contact electric field sensors, an electrical potential associated with two or more sections of an electrically active structure of the entity; accessing, from a database, data corresponding to past measurements of the electrically active structure taken utilizing non-resistive contact electric field sensors; electronically determining, by comparing data obtained from the repeated measuring to the accessed data, a current property of the electrically active structure of the entity; and generating, utilizing data obtained from the repeated measuring, a visualization of the electrically active structure of the entity, the visualization including a depiction of each of the two or more sections of the electrically active structure, together with a visualization of a typical state of the electrically active structure generated based on the accessed data.

Another aspect relates to a method comprising positioning one or more non-resistive contact electric field sensors proximate an entity; repeatedly measuring, utilizing the one or more non-resistive contact electric field sensors, an electrical potential associated with a structure of the entity; and generating, utilizing data obtained from the repeated measuring, a visualization of the entity.

In a feature of this aspect, the method includes using one or more properties of a sensor signal to inform on the position of the structure of the entity.

In a feature of this aspect, the method includes using one or more properties of a sensor signal to inform on the shape of the structure of the entity.

In a feature of this aspect, the method includes using one or more properties of a sensor signal to inform on the size of the structure of the entity.

In a feature of this aspect, the method includes using the amplitude of a sensor signal to inform on the position of the structure of the entity.

In a feature of this aspect, the method includes using the strength of a sensor signal to inform on the position of the structure of the entity.

In a feature of this aspect, the method comprises repeatedly repositioning the one or more non-resistive contact electric field sensors proximate the entity and determining a location of the structure of the entity based on progressive decay with distance from the source.

In a feature of this aspect, the method comprises isolating different waveforms by performing frequency analysis.

In a feature of this aspect, the method comprises applying bandwidth filters.

In a feature of this aspect, the structure of the entity comprises a brain, and the method comprises determining the relative power of different frequencies of brain voltage/time relations.

In a feature of this aspect, the method comprises utilizing known path information to inform on the structure or function of the structure of the entity.

In a feature of this aspect, the entity is an organ, and wherein the method comprises utilizing known path information to inform on the structure or function of the organ.

In a feature of this aspect, the method further includes utilizing external stimulus, and synchronizing the sensors with the external stimulus.

In a feature of this aspect, the method further includes utilizing external stimulus, and synchronizing the sensors with the external stimulus, repeatedly measuring the response to the external stimulus, and averaging measurement results to remove random noise.

In a feature of this aspect, the method includes one or more other interrogation modalities to inform, target, calibrate, and validate the electric field visualization.

In a feature of this aspect, other scanning modalities are utilized to identify electrical firing patterns.

In a feature of this aspect, functional magnetic resonance imaging (fMRI) is utilized to identify electrical firing patterns.

In a feature of this aspect, spectroscopy is utilized to identify electrical firing patterns.

In a feature of this aspect, the method includes repositioning at least one of the one or more sensors based on information obtained utilizing an imaging methodology.

In a feature of this aspect, sensor findings are verified utilizing ultrasound when visualizing the structure of the entity.

In a feature of this aspect, sensor findings are verified utilizing X-ray when visualizing the structure of the entity.

In a feature of this aspect, sensor findings are tuned utilizing ultrasound when visualizing the structure of the entity.

In a feature of this aspect, sensor findings are tuned utilizing X-ray when visualizing the structure of the entity.

In a feature of this aspect, the structure of the entity comprises a heart, and sensor findings are validated using another sensing modality.

In a feature of this aspect, the structure of the entity comprises a brain, and sensor findings are validated using another sensing modality.

In a feature of this aspect, the structure of the entity comprises one or more lungs, and sensor findings are validated using another sensing modality.

In a feature of this aspect, the structure of the entity comprises a gastrointestinal tract, and sensor findings are validated using another sensing modality.

In a feature of this aspect, the structure of the entity comprises one or more blood vessels, and sensor findings are validated using another sensing modality.

In a feature of this aspect, the method comprises detecting movement utilizing one or more accelerometers incorporated within or close to at least one of the one or more sensors.

In a feature of this aspect, the structure of the entity is a brain, and the method comprises utilizing Fourier analysis to separate different brain waves.

In a feature of this aspect, the structure of the entity is a brain, and the brain is visualized by assigning a different color to each of a plurality of different types of brain waves.

Another aspect relates to a method comprising positioning one or more non-resistive contact electric field sensors proximate an entity; repeatedly measuring, utilizing the one or more non-resistive contact electric field sensors, an electrical potential associated with a structure of the entity; and generating a visualization depicting structure or functionality of the structure of the entity based on data obtained from the repeated measuring.

In a feature of this aspect, the structure of the entity is a brain, and wherein the visualization includes a display of auras corresponding to different brain wave measurements, the thickness of each aura being in proportion to the amplitude of the type of wave it is associated with.

In a feature of this aspect, the structure of the entity is a brain, and in the visualization brain waves are represented as a set of simple sinusoidal waves with appropriate periods.

In a feature of this aspect, the structure of the entity comprises one or more lungs.

In a feature of this aspect, the method further includes utilizing one or more additional sensors of a different type.

In a feature of this aspect, the method further includes utilizing one or more additional non-perturbative sensors.

In a feature of this aspect, the method further includes utilizing one or more additional perturbative sensors.

In a feature of this aspect, the method further includes utilizing one or more sonar sensors.

In a feature of this aspect, the method further includes utilizing one or more sonar sensors for interrogation of the physical structure, shape, or form of the structure of the entity.

In a feature of this aspect, the method further includes utilizing one or more sonar sensors for interrogation of the physical structure, shape, or form of the structure of the entity by passive methods.

In a feature of this aspect, the method further includes utilizing one or more sonar sensors for interrogation of the physical structure, shape, or form of the structure of the entity by active methods.

In a feature of this aspect, one or more sonar sensors are utilized to locate and determine the characteristics of the structure of the entity.

In a feature of this aspect, one or more sonar sensors are utilized to inform the positioning of the one or more non-resistive contact electric field sensors.

In a feature of this aspect, one or more sonar sensors are utilized to inform on physical shape and distance and the one or more electric field sensors are utilized to inform on electric or magnetic characteristics and distance, and data from both types of sensors is utilized for cross-validation.

In a feature of this aspect, one or more sonar sensors are utilized to inform on physical shape and distance and the one or more electric field sensors are utilized to inform on electric or magnetic characteristics and distance, and data from both types of sensors is utilized for effective structural and functional imaging reconstruction.

In a feature of this aspect, the generated visualization includes an overlay generated based on data obtained from one or more sonar sensors.

In a feature of this aspect, one or more sonar sensors are utilized to ascertain fluid flow within the entity.

In a feature of this aspect, the method further includes utilizing one or more magnetometers.

In a feature of this aspect, the method further includes utilizing one or more magnetometers, data from the one or more magnetometers being utilized in combination with data from the one or more electric field sensors to generate the visualization.

In a feature of this aspect, the method further includes utilizing one or more cameras.

In a feature of this aspect, the method further includes utilizing one or more cameras, data from the one or more cameras being utilized in combination with data from the one or more electric field sensors to generate the visualization.

In a feature of this aspect, the method further includes utilizing one or more thermometers.

In a feature of this aspect, the method further includes utilizing one or more thermometers, data from the one or more thermometers being utilized in combination with data from the one or more electric field sensors to generate the visualization.

In a feature of this aspect, the method further includes utilizing one or more hydrometers.

In a feature of this aspect, the method further includes utilizing one or more hydrometers, data from the one or more hydrometers being utilized in combination with data from the one or more electric field sensors to generate the visualization.

In a feature of this aspect, the method further includes utilizing x-ray data.

In a feature of this aspect, the method further includes utilizing x-ray data in combination with data from the one or more electric field sensors to generate the visualization.

In a feature of this aspect, the method further includes utilizing computerized tomography processes.

In a feature of this aspect, computerized tomography processes are utilized in combination with data from the one or more electric field sensors to generate the visualization.

In a feature of this aspect, the method includes utilizing one or more electrometers.

In a feature of this aspect, impedance tomography data is utilized in generating the visualization.

In a feature of this aspect, the method further includes utilizing radar data.

In a feature of this aspect, the method further includes utilizing radar data in combination with data from the one or more electric field sensors to generate the visualization.

In a feature of this aspect, a visualization based on magnetic resonance signal data is overlaid over a visualization based on electric field sensor data.

In a feature of this aspect, the method further includes utilizing data from resistive contact electrometers in combination with data from the one or more electric field sensors to generate the visualization.

In a feature of this aspect, the method further includes utilizing data from a nuclear medical scanner in combination with data from the one or more electric field sensors to generate the visualization.

In a feature of this aspect, the method further includes utilizing spectroscopy data in combination with data from the one or more electric field sensors to generate the visualization.

In a feature of this aspect, the method further includes utilizing angiography data in combination with data from the one or more electric field sensors to generate the visualization.

In a feature of this aspect, the method further includes utilizing fluoroscopy data in combination with data from the one or more electric field sensors to generate the visualization.

Another aspect relates to a method comprising positioning one or more non-resistive contact electric field sensors proximate an entity; repeatedly measuring, utilizing the one or more non-resistive contact electric field sensors, an electrical potential associated with a first structure of the entity; obtaining, utilizing one or more additional sensors, data related to a second structure of the entity; generating a visualization depicting structure or functionality of one or more structures of the entity based on data obtained from the repeated measuring using the electric field sensors and based on data obtained utilizing the one or more additional sensors.

In a feature of this aspect, the first structure is associated with a first system of the entity and the second structure is associated with a second system of the entity.

Another aspect relates to a method comprising positioning one or more non-resistive contact electric field sensors proximate an entity; repeatedly measuring, utilizing the one or more non-resistive contact electric field sensors, an electrical potential associated with a first structure of the entity; obtaining, utilizing one or more additional sensors, data related to a plurality of other structures of the entity; and generating a visualization depicting structure or functionality of a plurality of systems of the entity based on data obtained from the repeated measuring using the electric field sensors and based on data obtained utilizing the one or more additional sensors.

In a feature of this aspect, the visualization depicts the entity's heart, respiratory system, and brain, as well as skeletal muscle of the entity.

Another aspect relates to a method comprising positioning one or more non-resistive contact electric field sensors proximate an entity; repeatedly measuring, utilizing the one or more non-resistive contact electric field sensors, an electrical potential associated with a component of the entity; tracking the movement of a component of the entity by analyzing the change in electric field as it runs through the anatomical structure of the component; and generating a visualization depicting movement of the component based on the analysis of the change in electric field as it runs through the anatomical structure of the component.

Another aspect relates to a method comprising positioning a plurality of non-resistive contact electric field sensors proximate an entity, each sensor being positioned proximate a respective region of the entity and being referenced to that region; repeatedly measuring, utilizing the one or more non-resistive contact electric field sensors, an electrical potential associated with the entity; and generating, utilizing data obtained from the repeated measuring, a visualization of the entity, the visualization including a depiction of the regions of the entity.

Another aspect relates to a method comprising repeatedly measuring, utilizing one or more moving non-resistive contact electric field sensors engaged in a mobile scanning mode, an electrical potential associated with a structure of an entity; and generating, utilizing data obtained from the repeated measuring, a visualization of the structure of the entity.

In a feature of this aspect, the structure of the entity includes two or sections, and wherein the generated visualization depicts the two or more sections.

In a feature of this aspect, the visualization utilizes fixed shapes.

In a feature of this aspect, the visualization utilizes variable shapes.

In a feature of this aspect, the visualization utilizes colors.

In a feature of this aspect, the visualization utilizes two-dimensional displays.

In a feature of this aspect, the visualization utilizes three dimensional displays.

In a feature of this aspect, the visualization utilizes sound.

In a feature of this aspect, the visualization is static.

In a feature of this aspect, the visualization is dynamic.

In a feature of this aspect, the visualization utilizes texture.

In a feature of this aspect, the visualization utilizes heat.

In a feature of this aspect, the visualization utilizes holograms.

In a feature of this aspect, the visualization comprises video.

Another aspect relates to a method comprising repeatedly measuring, utilizing one or more non-resistive contact electric field sensors, a geoelectric displacement signature of a moving entity; and generating, utilizing data obtained from the repeated measuring, a visualization of the entity.

Another aspect relates to a method comprising repeatedly measuring, utilizing one or more moving non-resistive contact electric field sensors, a geoelectric displacement signature of an entity; and generating, utilizing data obtained from the repeated measuring, a visualization of the entity.

Another aspect relates to a method comprising positioning one or more non-resistive contact electric field sensors proximate an entity; repeatedly measuring, utilizing the one or more non-resistive contact electric field sensors, an electrical potential associated with a structure of the entity; and generating a visualization depicting structure or functionality of the structure of the entity based on data obtained from the repeated measuring; wherein the visualization comprises a three dimensional visualization.

Another aspect relates to a system configured for performance of a disclosed method.

Another aspect relates to a system comprising a plurality of non-resistive contact electric field sensors arranged at an entity, each of the plurality of non-resistive contact electric field sensors being positioned proximate a different particular generally predetermined location; wherein the system is configured to repeatedly measure, utilizing the plurality of non-resistive contact electric field sensors, an electrical potential associated with a structure of the entity, and generate, utilizing data obtained from the repeated measuring, a visualization of the structure of the entity.

Another aspect relates to a system comprising a plurality of non-resistive contact electric field sensors arranged at an entity, each of the plurality of non-resistive contact electric field sensors being positioned proximate a different particular generally predetermined location; one or more computer readable media containing computer executable instructions configured to repeatedly measure, utilizing the plurality of non-resistive contact electric field sensors, an electrical potential associated with two or more sections of a structure of the entity, and generate, utilizing data obtained from the repeated measuring, a visualization of the structure of the entity, the visualization including a depiction of each of the two or more sections of the structure.

Another aspect relates to a system comprising a plurality of non-resistive contact electric field sensors arranged at an entity, each of the plurality of non-resistive contact electric field sensors being positioned proximate a different particular generally predetermined location; wherein the system is configured to repeatedly measure, utilizing the plurality of non-resistive contact electric field sensors, an electrical potential associated with two or more sections of a structure of the entity, and generate, utilizing data obtained from the repeated measuring, a visualization of the structure of the entity, the visualization including a depiction of each of the two or more sections of the structure.

Another aspect relates to a system comprising a plurality of non-resistive contact electric field sensors arranged at an entity, each of the plurality of non-resistive contact electric field sensors being positioned proximate a different particular generally predetermined location; one or more additional sensors; wherein the system is configured to repeatedly measure, utilizing the plurality of non-resistive contact electric field sensors, an electrical potential associated with a structure of the entity, and generate, utilizing data obtained from the repeated measuring and data obtained from the one or more additional sensors, a visualization of at least a portion of the entity.

In a feature of this aspect, the one or more additional sensors comprise a sonar sensor.

In a feature of this aspect, the one or more additional sensors comprise an electrometer.

In a feature of this aspect, the one or more additional sensors comprise a magnetometer.

In a feature of this aspect, the one or more additional sensors comprise a camera.

In a feature of this aspect, the one or more additional sensors comprise a thermometer.

In a feature of this aspect, the one or more additional sensors comprise a hydrometer.

In a feature of this aspect, the one or more additional sensors comprise a resistive contact electrometer.

In addition to the herein described aspects and features of the present invention, it should be noted that the present invention additionally encompasses the various possible combinations and subcombinations of such aspects and features. Thus, for example, any described aspect may be combined with any described feature in accordance with the present invention without requiring any other aspect or feature.

BRIEF DESCRIPTION OF THE DRAWINGS

One or more preferred embodiments of the present invention now will be described in detail with reference to the accompanying drawings, wherein the same elements are referred to with the same reference numerals, and wherein.

DETAILED DESCRIPTION

Figure 1:
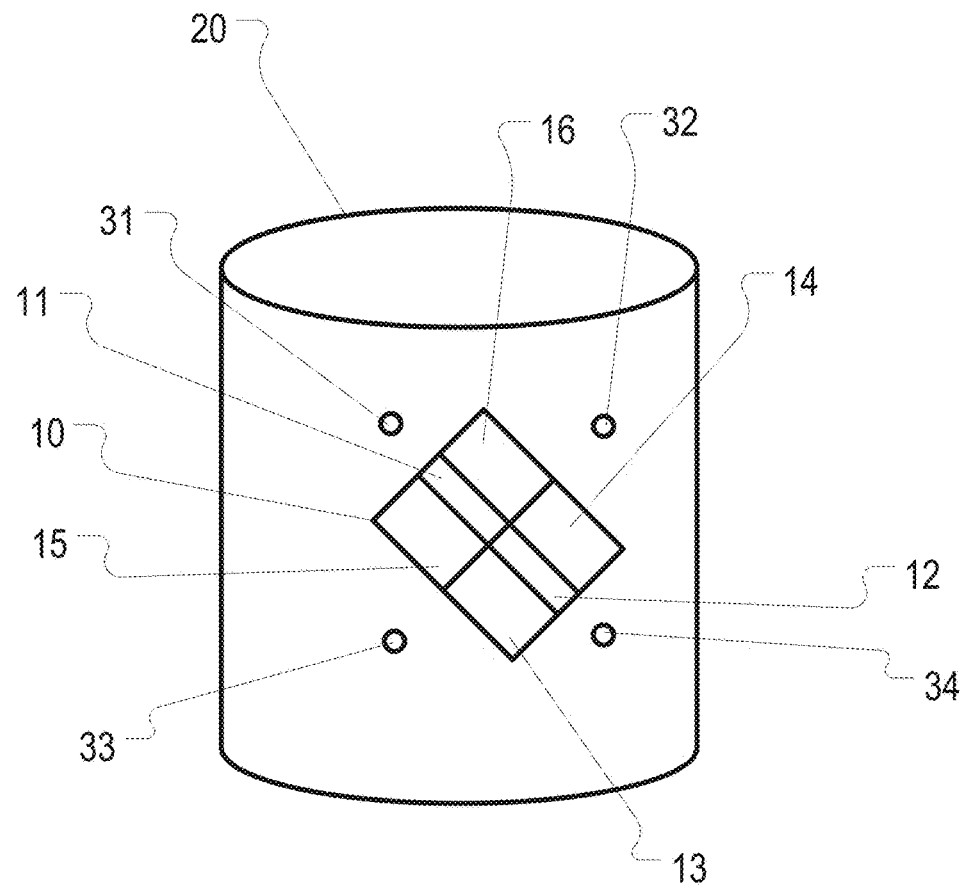
FIG. 1 schematically illustrates an exemplary electrically active structure.

As a preliminary matter, it will readily be understood by one having ordinary skill in the relevant art ("Ordinary Artisan") that the present invention has broad utility and application. As should be understood, any embodiment may incorporate only one or a plurality of the above-disclosed aspects of the invention and may further incorporate only one or a plurality of the above-disclosed features. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. §112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, one or more preferred embodiments of the present invention are next described. The following description of one or more preferred embodiments is merely exemplary in nature and is in no way intended to limit the invention, its implementations, or uses.

One or more preferred implementations relate to methods by which non-resistive contact sensors are used exclusively or in combination with other sensors and the sensor data is utilized for detecting properties of one or more biological or non-biological entities.

In some preferred implementations intended for use with biological entities, a method utilizes an electric field sensor or sensors for the measurement of the structural and functional characteristics of organs and other structures where the electric field sensor does not have resistive contact with the organism, conferring multiple advantages. More particularly, one or more preferred implementations relate to sensors and sensor systems including devices and installations for assemblies for detecting structural and functional signatures associated with electric potentials that may also detect a displacement signature within the geoelectric field, and/or specific components and/or structures that are a component of that entity or entities. Specifically there is no resistive contact between the entity and the signal transduction component of the electric field sensor or sensors. Other sensor types may be added in to provide further information such as for the identification of that entity or for further interrogation or validation of the structure and function of that entity.

One or more preferred implementations relate to a novel monitoring technology using an electric field sensor or sensors that does not have resistive contact with an entity, such as, for example, an organism, being monitored. For example, in one or more preferred implementations, limitations of conventional diagnostic systems can be obviated through the implementation of non-conductive passive electric field sensors. Additionally, in combination with other sensor types, there is the opportunity to create highly advanced imaging systems.

The lack of resistive contact allows the electric potentials associated with the organs to be measured without drawing current away from the entity. Furthermore, the lack of resistive contact allows the geoelectric displacement signature of the entity to be measured if either the entity or the sensor or sensors are moving.

In preferred implementations, an electric field sensor enables interrogation of the electric and/or magnetic potential associated with structures or the physical displacement of the geo-electric field by an entity. The electric potential sensor signal transduction has no resistive contact with the entity.

In one or more preferred implementations, an electric potential sensor including a signal transduction component is implanted or temporarily placed within an entity with a membrane or structure separating the signal transduction component of the sensor (and possibly the entire sensor) from the substance of the entity.

One or more preferred implementations relate to a transfer solution where what is happening electrically in real physical space is detected by electrical field sensors in sensor space that is then transposed into an image or set of images in visualization space.

FIG. 1 schematically illustrates an exemplary electrically active structure 10 in real physical space. Although the electrically active structure 10 is just a schematic illustration, in one or more preferred implementations such electrically active structure 10 might represent a human heart or other biological structure. The electrically active structure includes components 11,12,13,14,15,16.

This electrically active structure 10 lies in a containing structure 20, which is schematically illustrated in FIG. 1 as a cylinder. Returning to exemplary implementations in which the electrically active structure 10 represents a human heart, such containing structure 20 might represent a human torso, or thorax. The containing structure 20 allows electric field transmission that is detected by four non-resistive contact electrodes 31,32,33,34 (although it will be appreciated that four is merely an exemplary number).

In a preferred methodology, the non-resistive contact electrodes 31,32,33,34 are placed relative to landmarks on the containing structure 20 in a manner designed to keep the spatial relations of the non-resistive contact electrodes 31,32,33,34 constant among different containing structures of that type, e.g. among different torsos. In an exemplary preferred torso implementation, non-resistive contact electrode 31 might be placed proximate the sternal notch, non-resistive contact electrode 32 might be placed proximate the third rib at the anterior axillary line on the left, non-resistive contact electrode 33 might be placed proximate the xiphoid process, and non-resistive contact electrode 34 might be placed proximate the seventh rib at the anterior axillary line on the left.

Figure 2A:
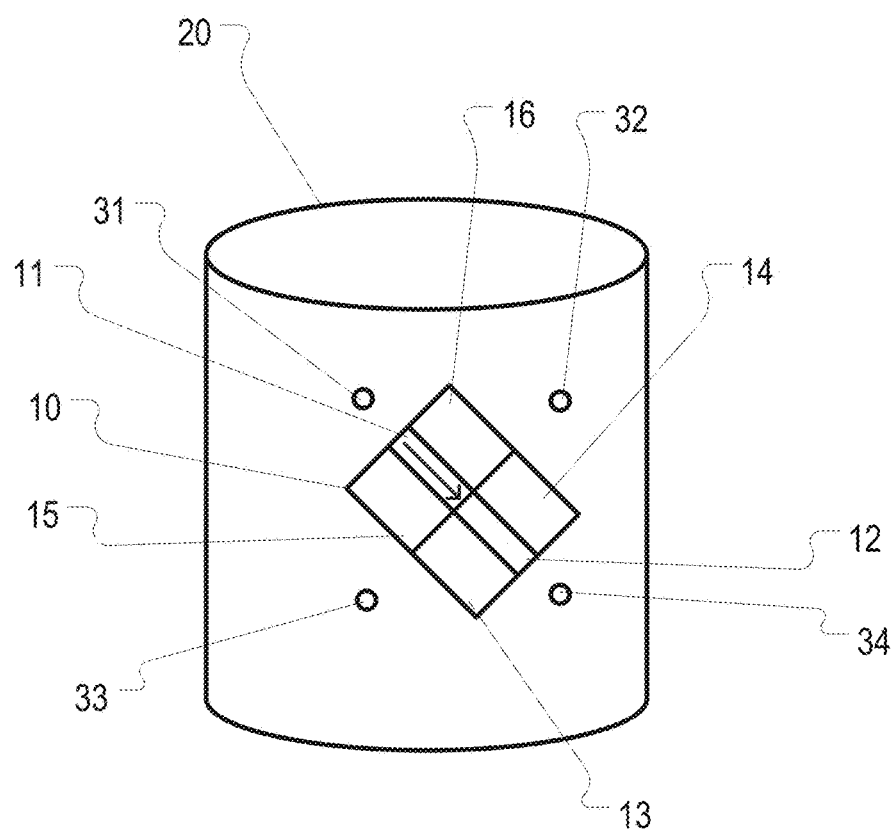
FIGS. 2A-D schematically illustrate electric current flow through the electrically active structure of FIG. 1.
Figure 2B:
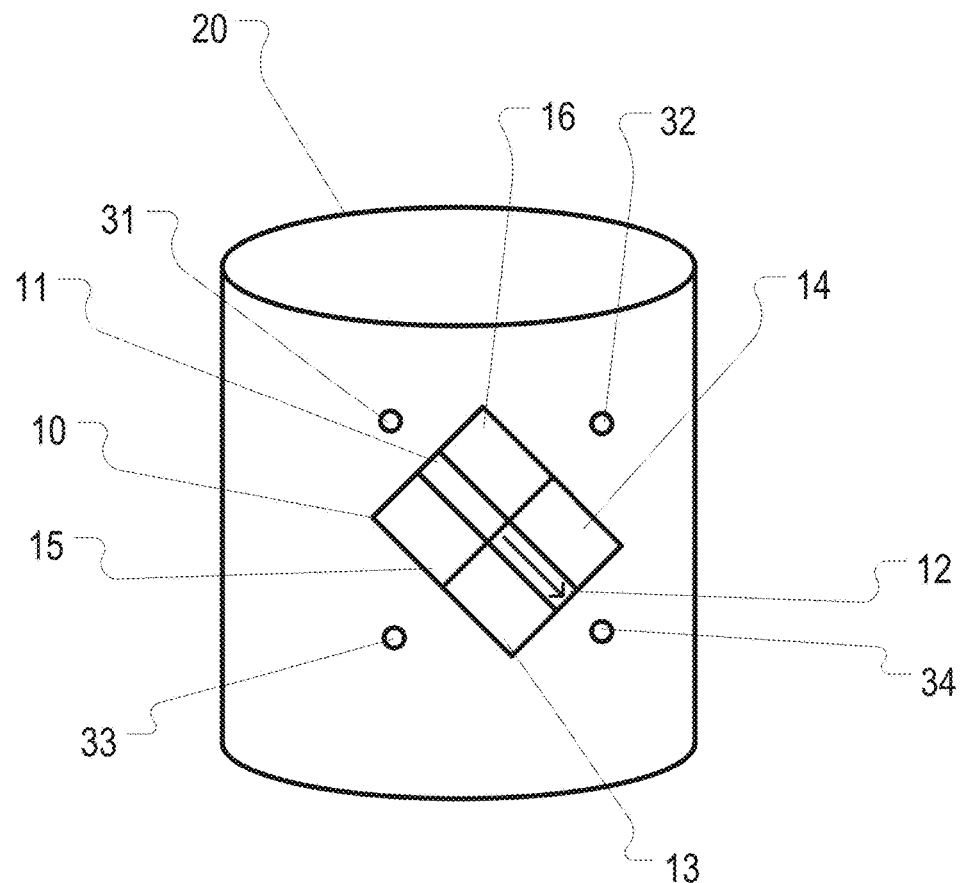
Figure 2C:
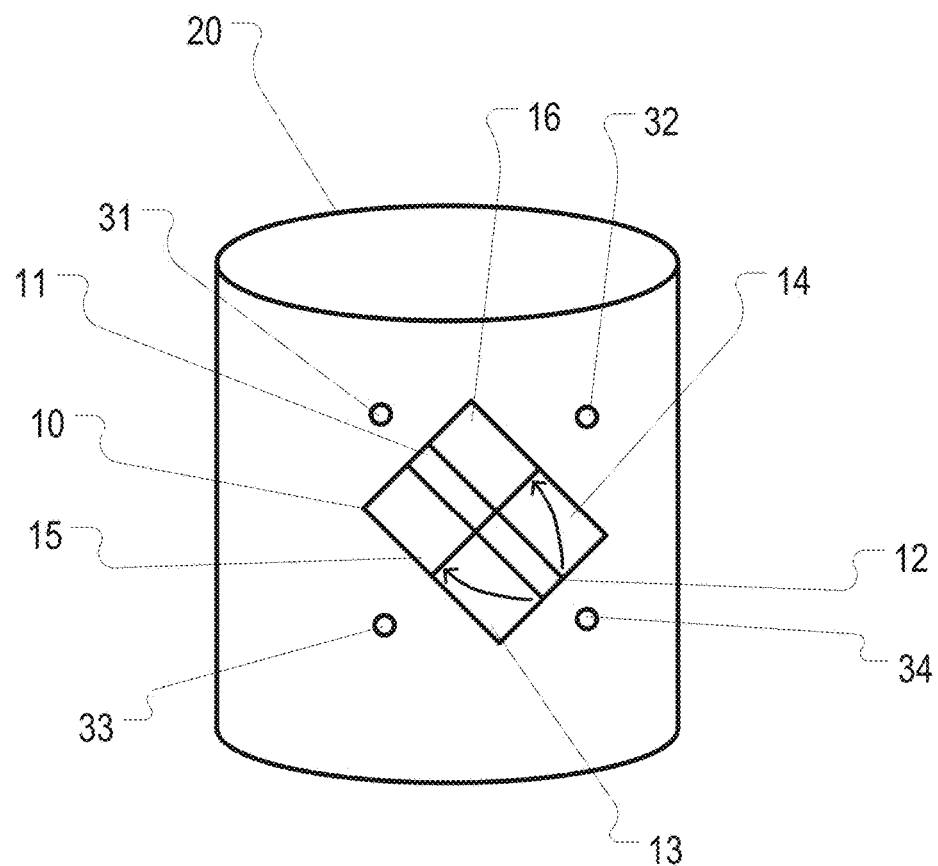
Figure 2D:
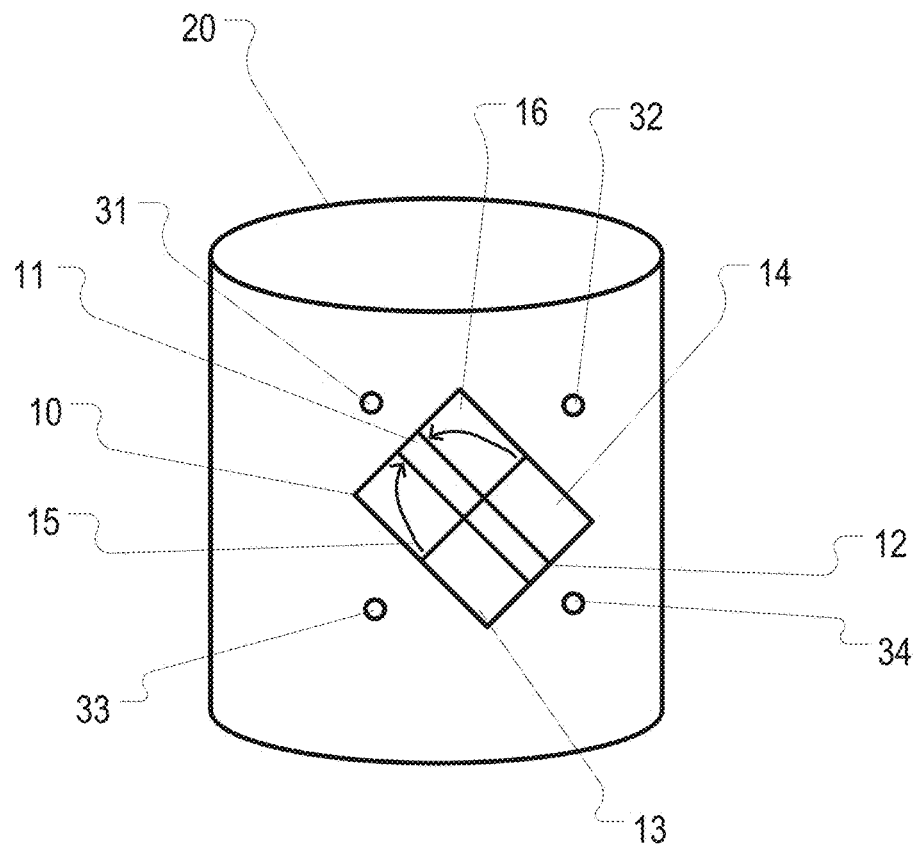

In this preferred implementation, an electrical current flows through each of the components 11,12,13,14,15,16 of the electrically active structure 10 and cycles through at various time points. This electrical current flow is illustrated in FIGS. 2A-D by arrows. Each of the figures schematically illustrates exemplary electrical flow from a first time point t1 to a next time point t2. FIG. 2A schematically illustrates exemplary electrical flow from time t=i to time t=ii; FIG. 2B schematically illustrates exemplary electrical flow from time t=ii to time t=iii; FIG. 2C schematically illustrates exemplary electrical flow from time t=iii to time t=iv; and FIG. 2D schematically illustrates exemplary electrical flow from time t=iv to a subsequent time point, which can once again be characterized as time t=i.

Figure 3:
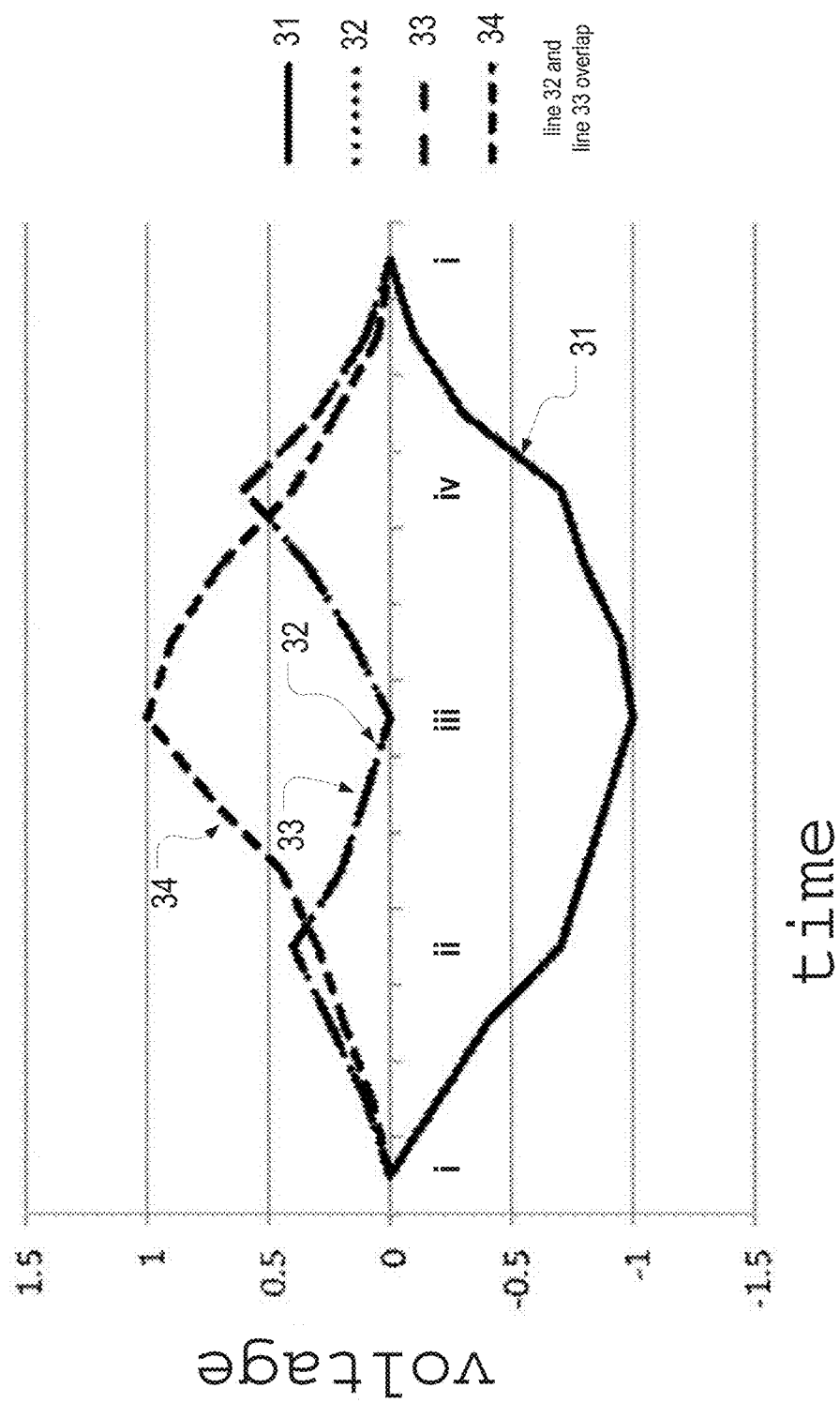
FIG. 3 illustrates a line graph depicting an active electric field produced by an electric current over time.

FIG. 3 illustrates a line graph depicting the active electric field produced by the electric current over time. This line graph can be characterized as depicting sensor space b.

At time i, all electrodes record a zero (0) potential difference (voltage). As charge flows away from the electrode 31 in the component 11, there is a steep negative voltage over time due to the dipole being adjacent to and directly away from the electrode 31. For the electrode 32 and the electrode 33, there is a shallow increase in voltage as the charge moves towards them through the component 11. For the electrode 34, the charge flow is directly towards the electrode 34, though further away so the voltage deflection is relatively weak (though positive).

As the current flows through component 12, the voltage deflection at electrode 31 is still negative though not as steep due to the distance away from the source. For the electrode 32 and the electrode 33, the deflection is now negative and again relatively shallow as the dipoles are at an angle away from the electrodes. For the electrode 34, the positive deflection becomes steeper as the electric field source moves directly towards and closer.

Once the current hits the apex of the structure at the edge of the component 12, it starts flowing back through the component 13 and the component 14. The current flowing through these components 13,14 is now flowing back towards the electrode 31, though on an angular course so the positive voltage is initially at less of an angle than the previous negative voltage. At the electrode 32 and the electrode 33, the current is flowing more directly towards them producing a steeper positive change in electric field. For the electrode 34, the current is flowing away and again in an angular manner so there is less negative deflection. As current flow through the component 15 and the component 16 towards their source there is an increasingly positive deflection at the electrode 31, apart from at the end where it shallows off and is travelling at an angular vector. At the electrode 32 and the electrode 33, the voltage deflection is negative and steeper than at the electrode 34, where the current is further from and angular to the source.

Figure 4:
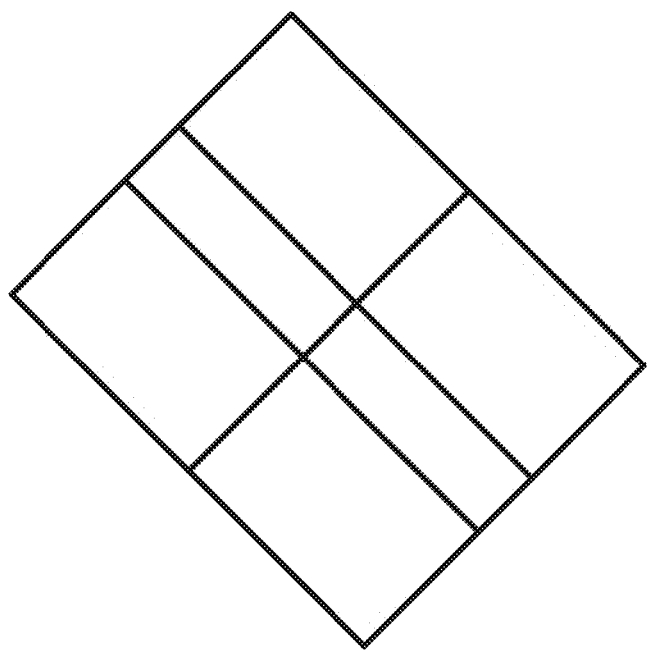
FIG. 4 illustrates a visualization of the electrically active structure of FIG. 1.

For the purposes of illustration, this exemplary illustrated scenario is taken as normal electrical flow in a normal electrically active structure and illustrated by six blocks in FIG. 4. This figure can be characterized as depicting a visualization of the electrically active structure 10 in a visualization space c.

By ascertaining such normal flow through the components of the structure (that may be an approximate representation of a heart), where the electrodes are placed in relation to landmarks on the containing structure (that may represent a human torso), a standard visualization of this data can be produced from graphical images. The current can be shown to flow through the structure (e.g. the heart) and can be synced in time with the various measurements at the electrodes as described above.

In one or more preferred implementations, if an individual has a larger electrically active structure (e.g. a larger heart) than normal, this could be ascertained by utilizing a database containing data on normal electrically active structures (e.g. normal hearts), and the larger structure could be represented as larger in a visual depiction of the electrically active structure in a containing structure. This could be represented as a static or moving image.

Figure 5:
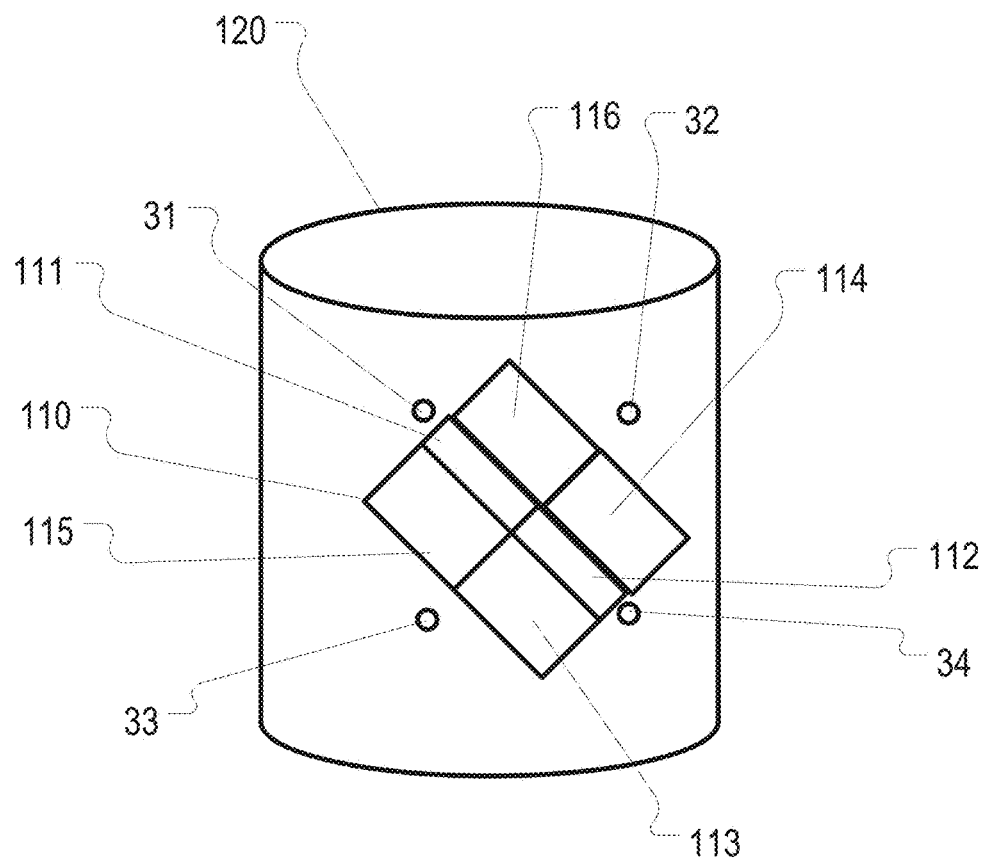
FIG. 5 schematically illustrates another exemplary electrically active structure.
Figure 6A:
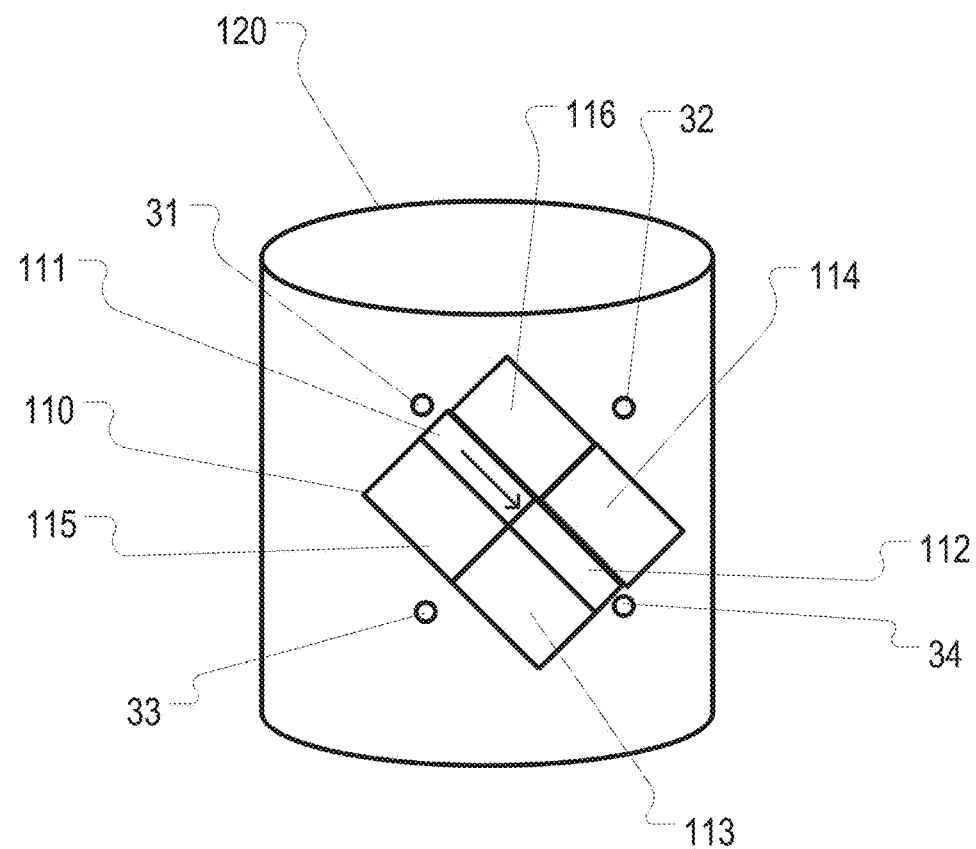
FIGS. 6A-D schematically illustrate electric current flow through the electrically active structure of FIG. 5.
Figure 6B:
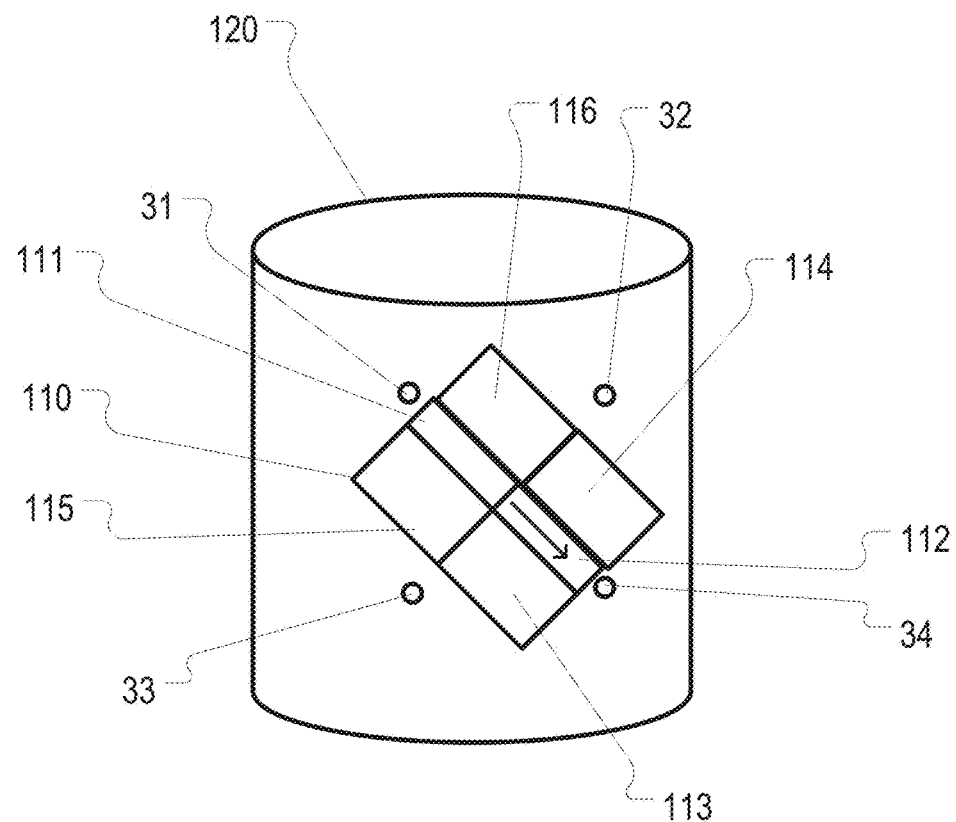
Figure 6C:
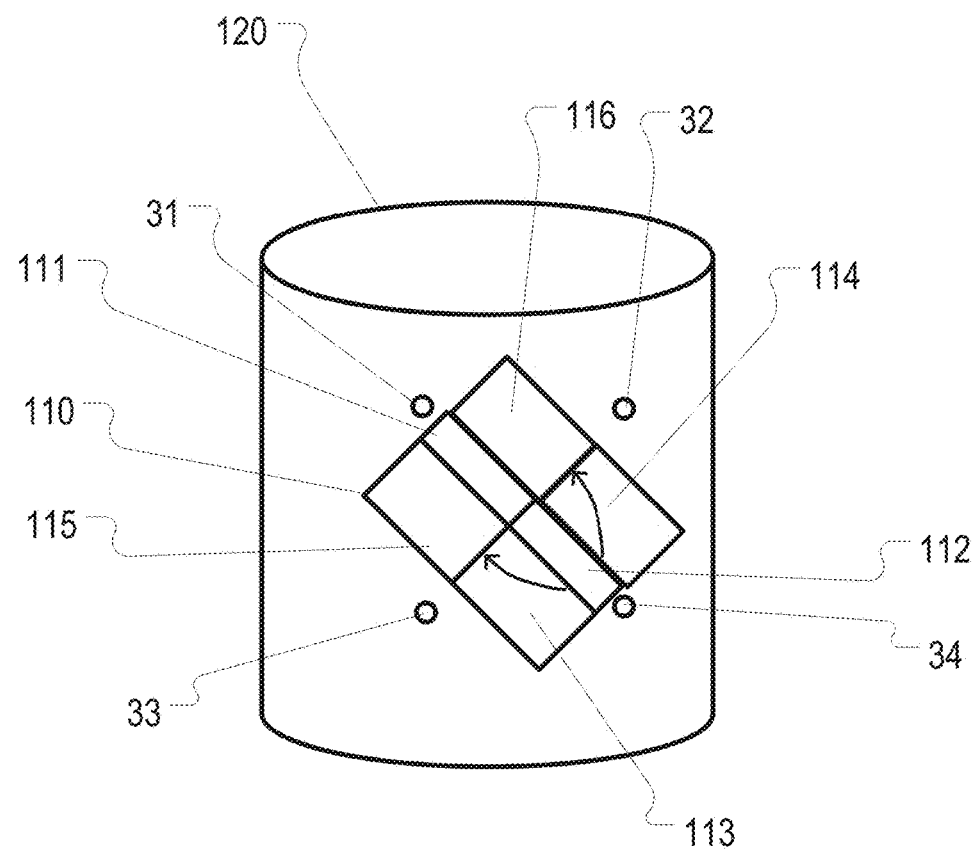
Figure 6D:
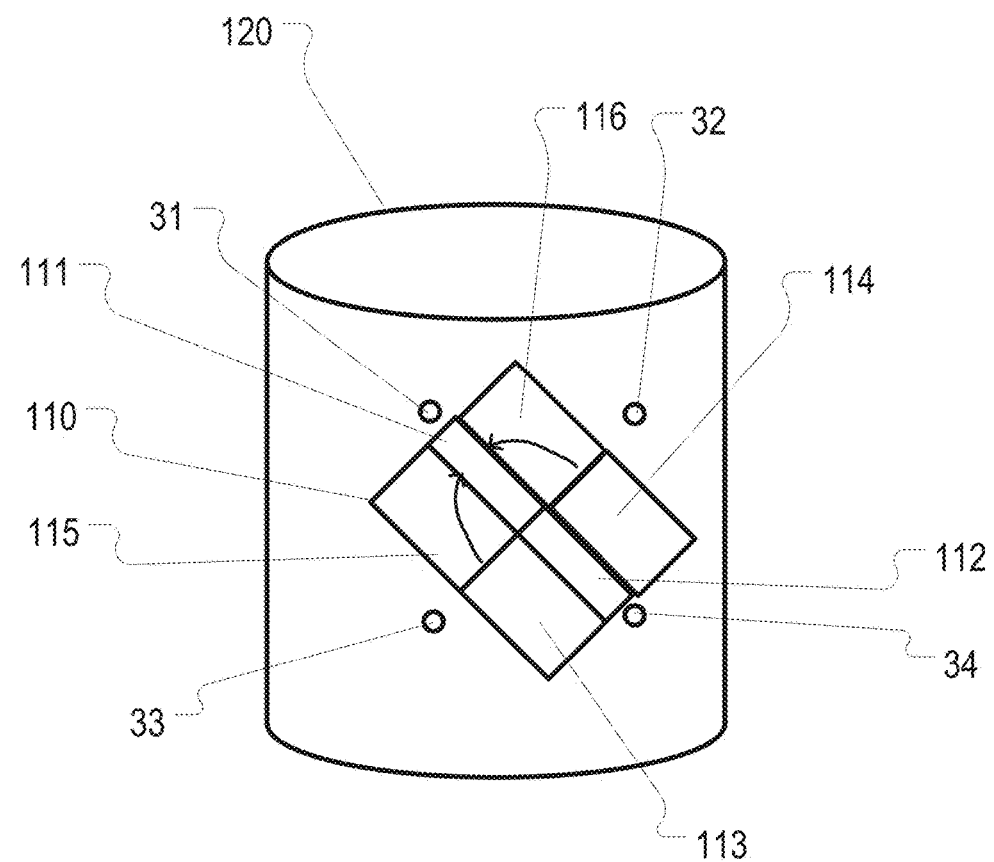
Figure 7:
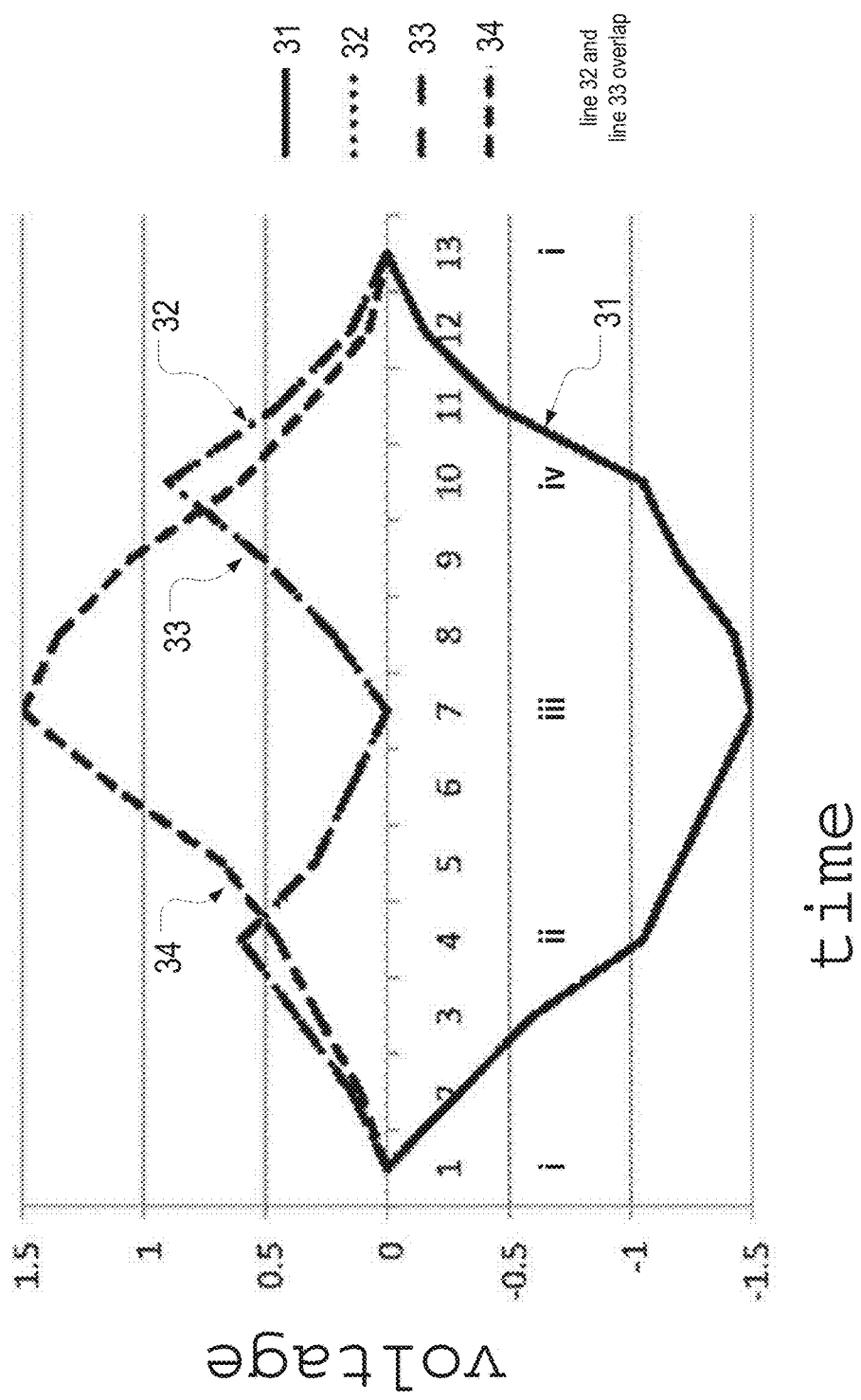
FIG. 7 illustrates a line graph depicting an active electric field produced by an electric current over time.
Figure 8:
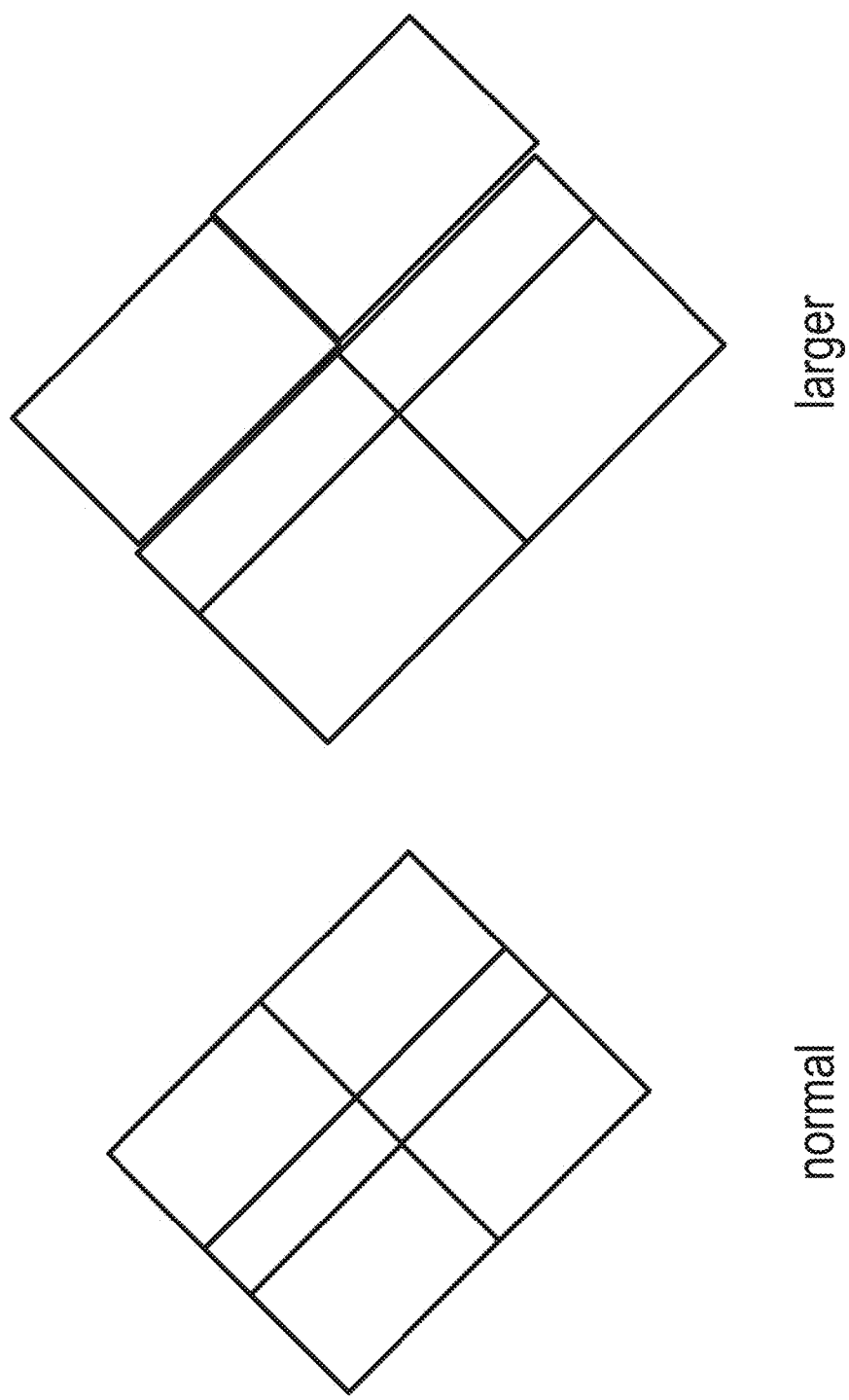
FIG. 8 illustrates a visualization of the electrically active structure of FIG. 5.

FIG. 5 illustrates an exemplary larger electrically active structure 110 including components 111,112,113,114,115, 116 lying in containing structure 120. Exemplary electrical current flow through each of the components 111,112,113, 114,115,116 is illustrated in FIGS. 6A-D by arrows. Each of the figures schematically illustrates exemplary electrical flow from a first time point t1 to a next time point t2. FIG. 6A schematically illustrates exemplary electrical flow from time t=i to time t=ii; FIG. 6B schematically illustrates exemplary electrical flow from time t=ii to time t=iii; FIG. 6C schematically illustrates exemplary electrical flow from time t=iii to time t=iv; and FIG. 6D schematically illustrates exemplary electrical flow from time t=iv to a subsequent time point, which can once again be characterized as time t=i. FIG. 7 illustrates a line graph depicting the active electric field produced by the electric current over time, and FIG. 8 depicts a visualization of the larger electrically active structure 110 in a visualization space c compared to a normal electrically active structure 10.

Figure 9:
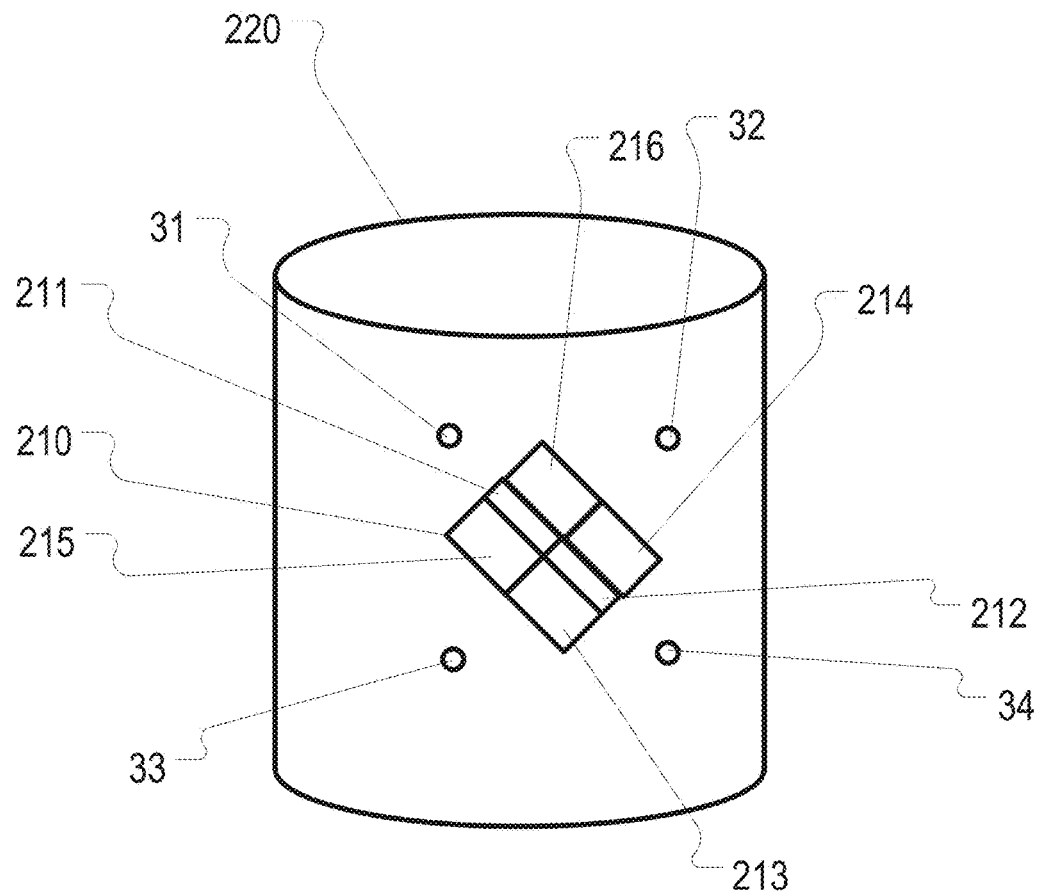
FIG. 9 schematically illustrates another exemplary electrically active structure.
Figure 10A:
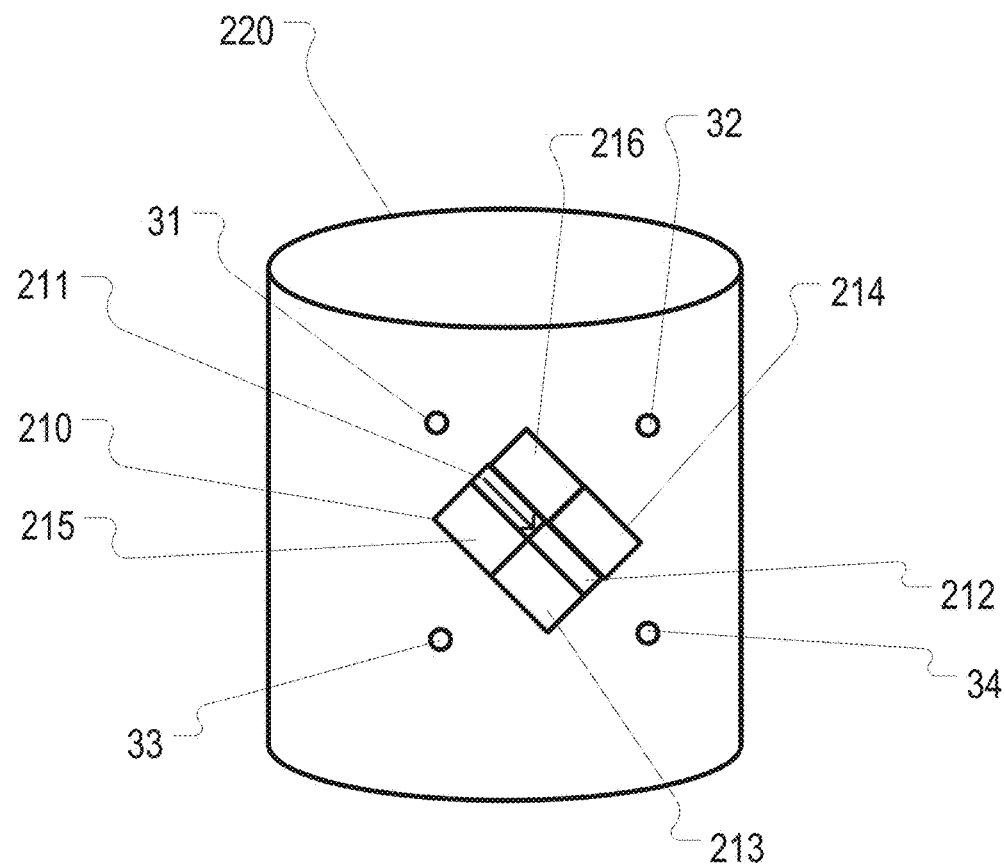
FIGS. 10A-D schematically illustrate electric current flow through the electrically active structure of FIG. 9.
Figure 10B:
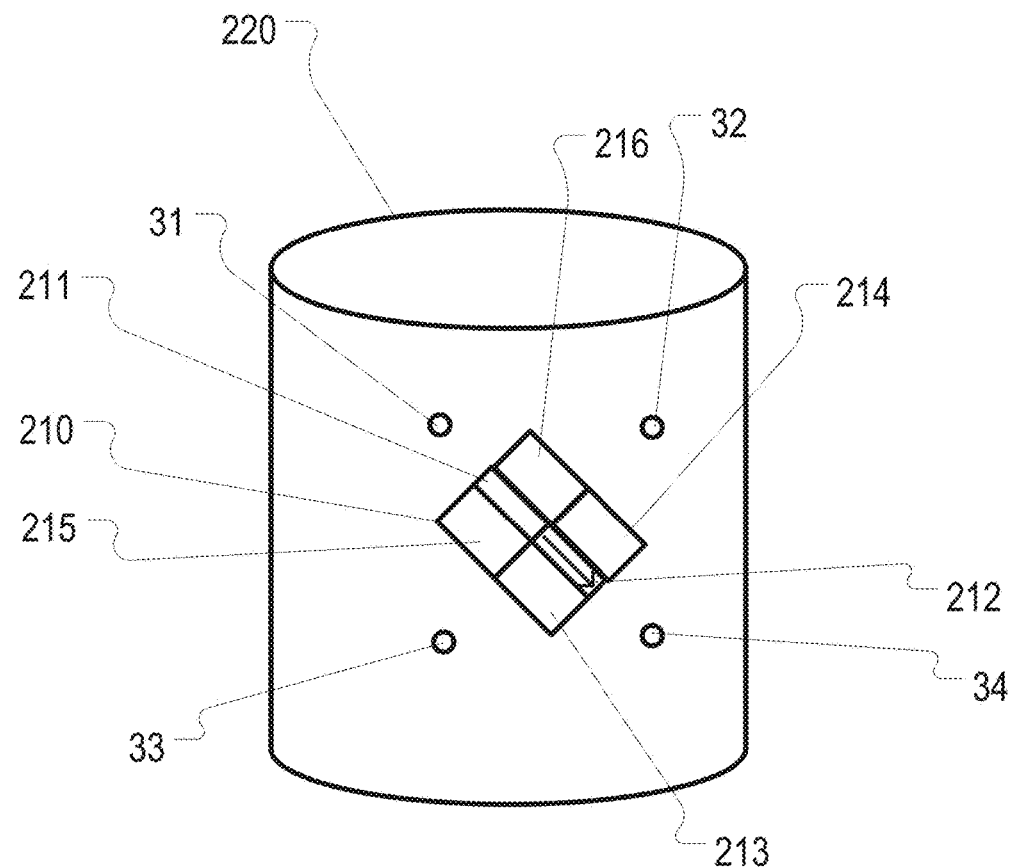
Figure 10C:
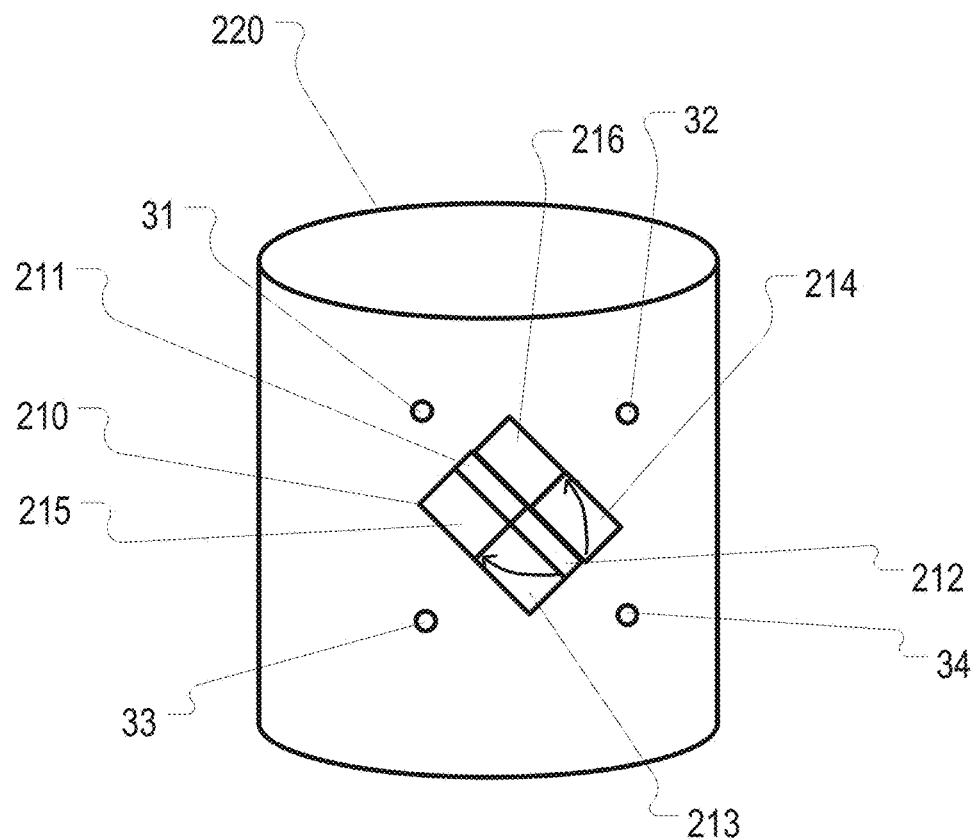
Figure 10D:
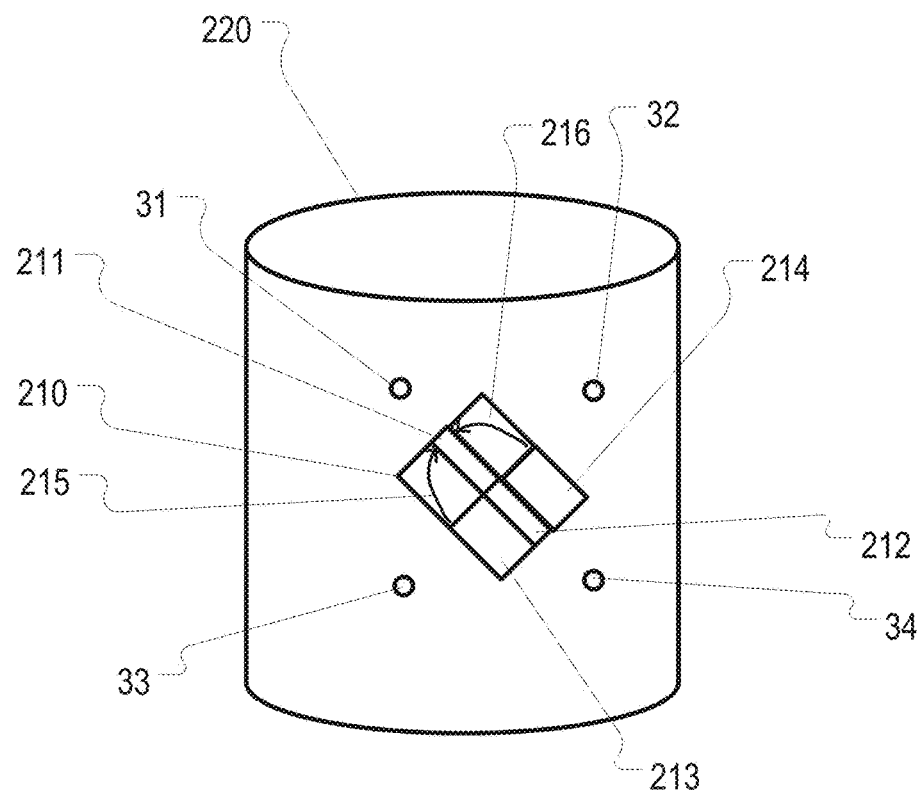
Figure 11:
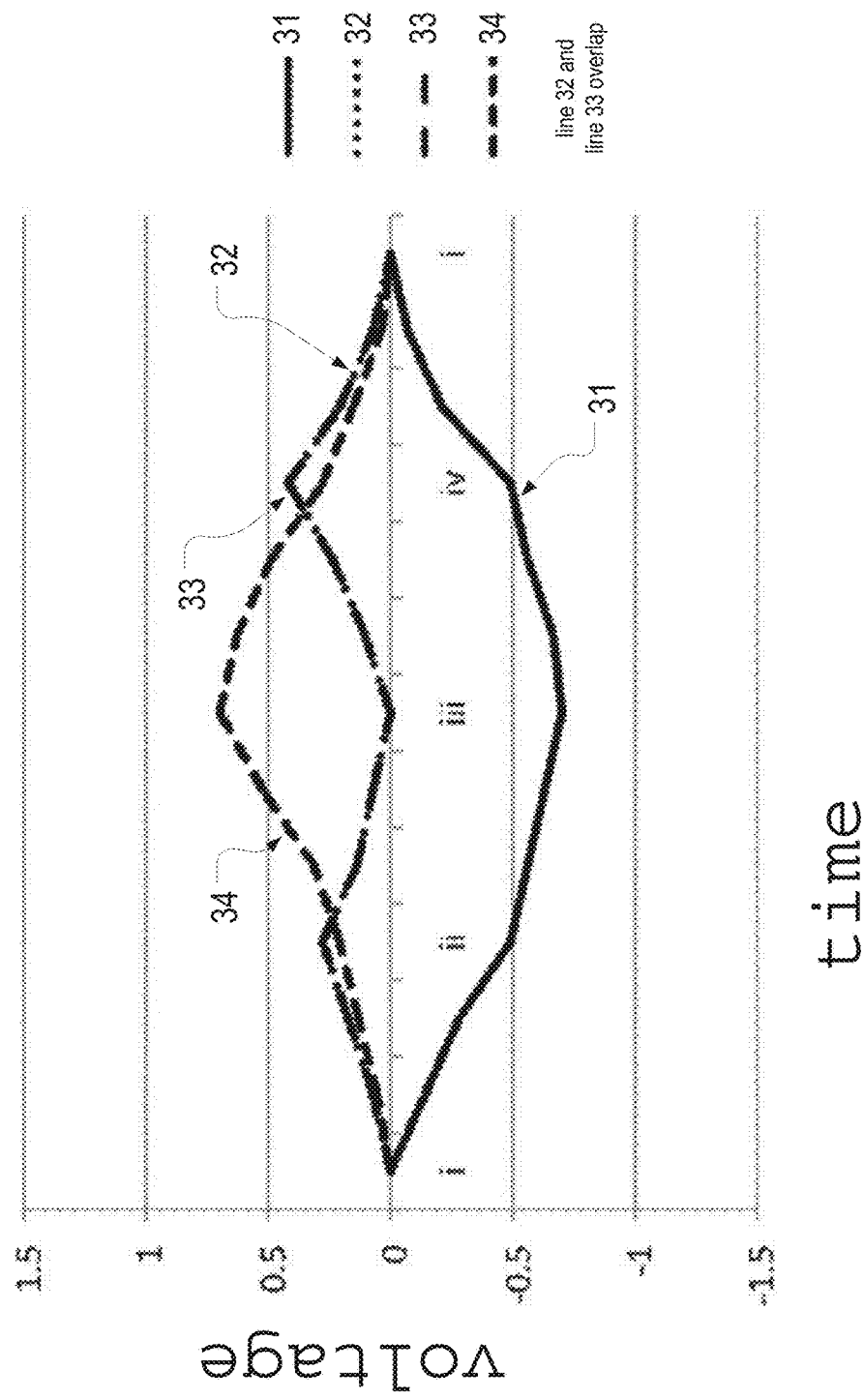
FIG. 11 illustrates a line graph depicting an active electric field produced by an electric current over time.
Figure 12:
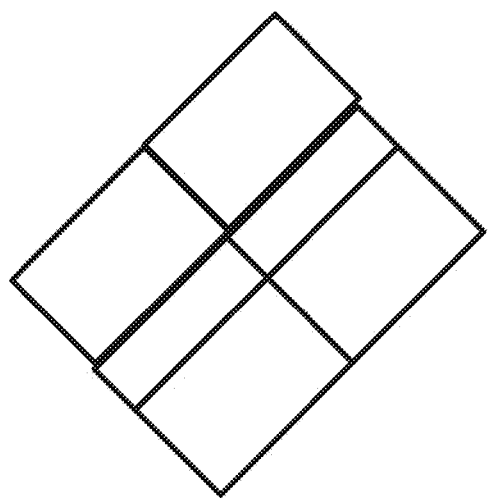
FIG. 12 illustrates a visualization of the electrically active structure of FIG. 9.
Figure 12:
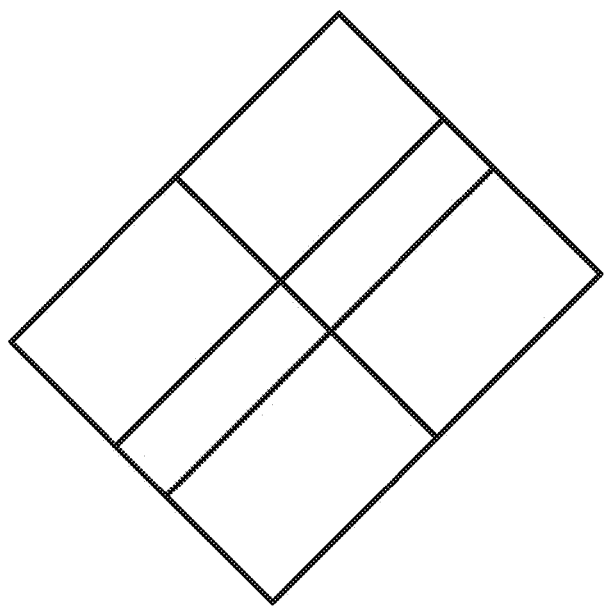

The converse applies if the voltages were low and patterns were changed representing a smaller electrically active structure. FIG. 9 illustrates an exemplary smaller electrically active structure 210 including components 211,212,213,214, 215,216 lying in containing structure 220. Exemplary electrical current flow through each of the components 211,212, 213,214,215,216 is illustrated in FIGS. 10A-D by arrows. Each of the figures schematically illustrates exemplary electrical flow from a first time point t1 to a next time point t2. FIG. 10A schematically illustrates exemplary electrical flow from time t=i to time t=ii; FIG. 10B schematically illustrates exemplary electrical flow from time t=ii to time t=iii; FIG. 10C schematically illustrates exemplary electrical flow from time t=iii to time t=iv; and FIG. 10D schematically illustrates exemplary electrical flow from time t=iv to a subsequent time point, which can once again be characterized as time t=i. FIG. 11 illustrates a line graph depicting the active electric field produced by the electric current over time, and FIG. 12 depicts a visualization of the smaller electrically active structure 210 in a visualization space c compared to a normal electrically active structure 10.

Figure 13:
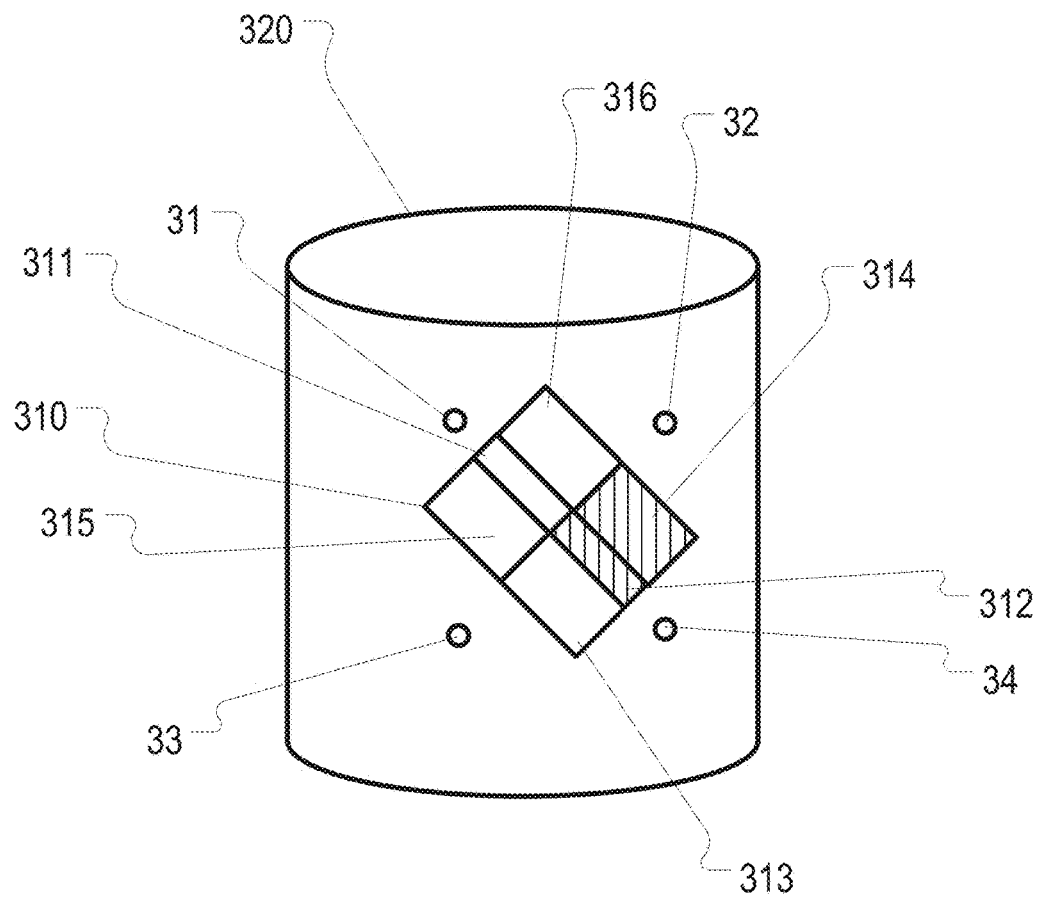
FIG. 13 schematically illustrates another exemplary electrically active structure.
Figure 14A:
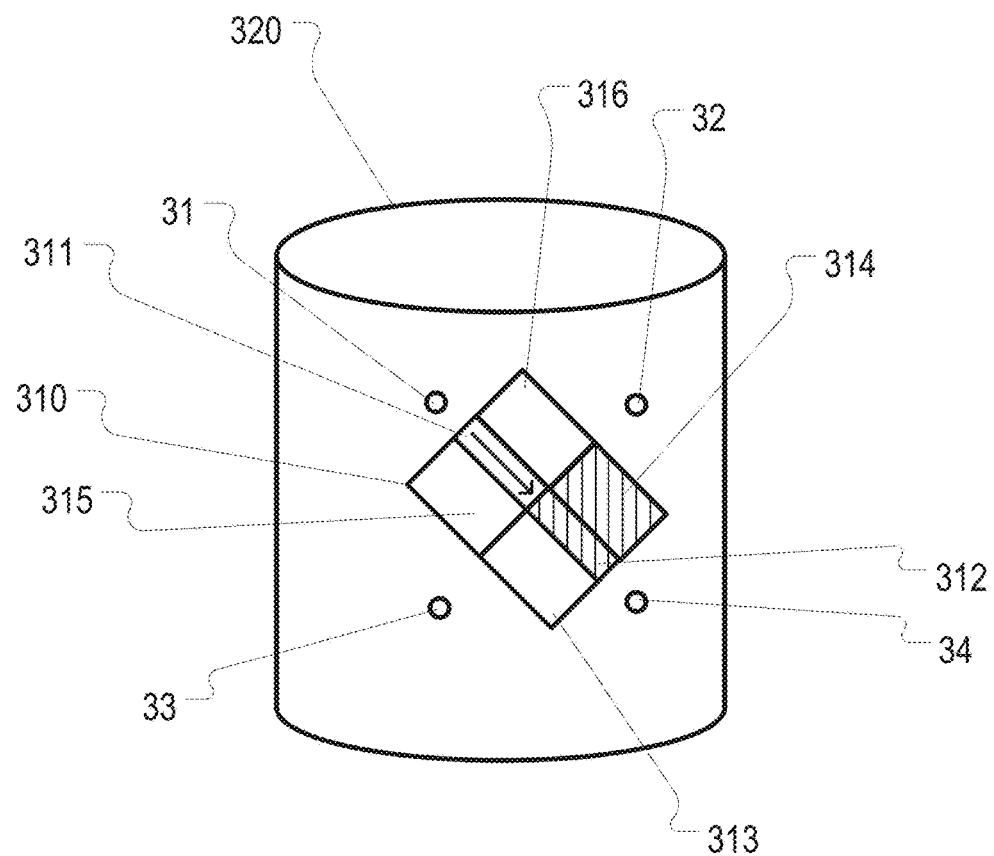
FIGS. 14A-D schematically illustrate electric current flow through the electrically active structure of FIG. 13.
Figure 14B:
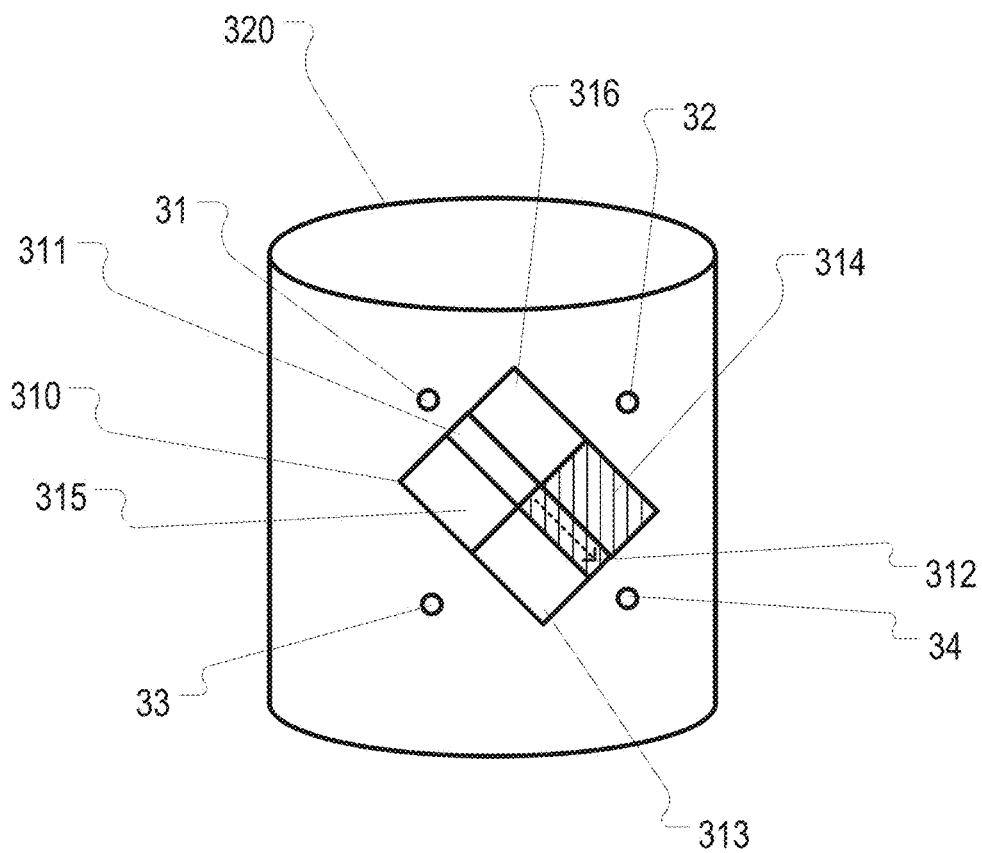
Figure 14C:
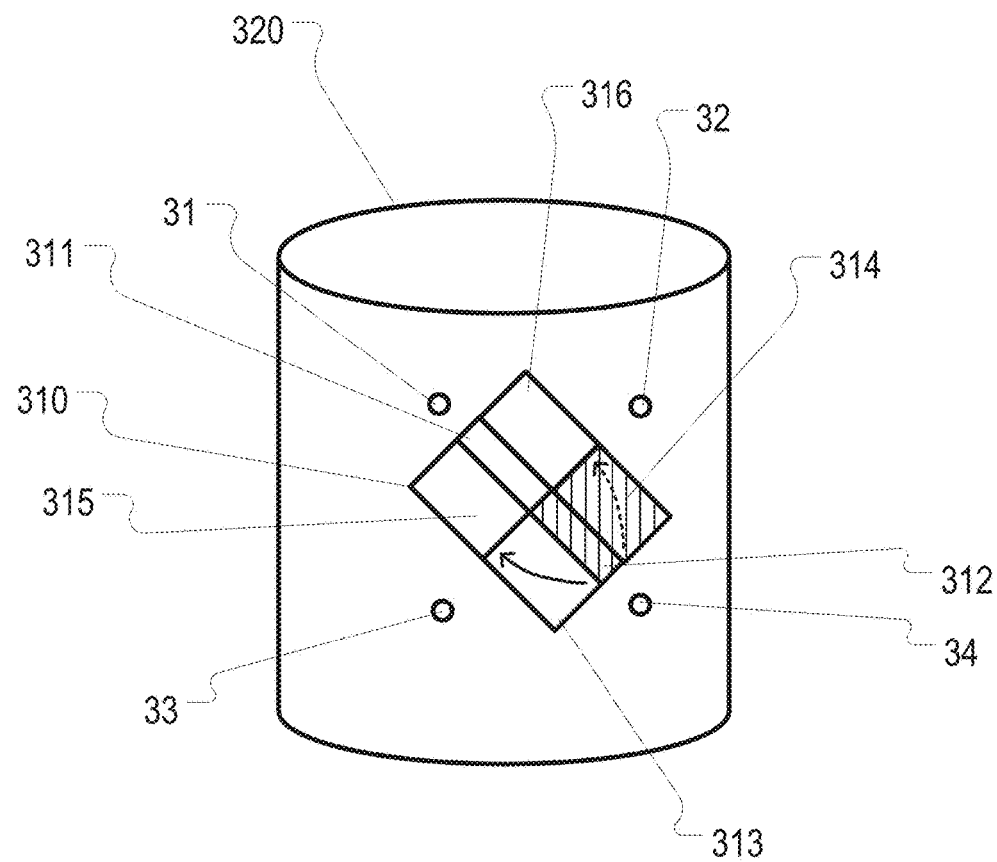
Figure 14D:
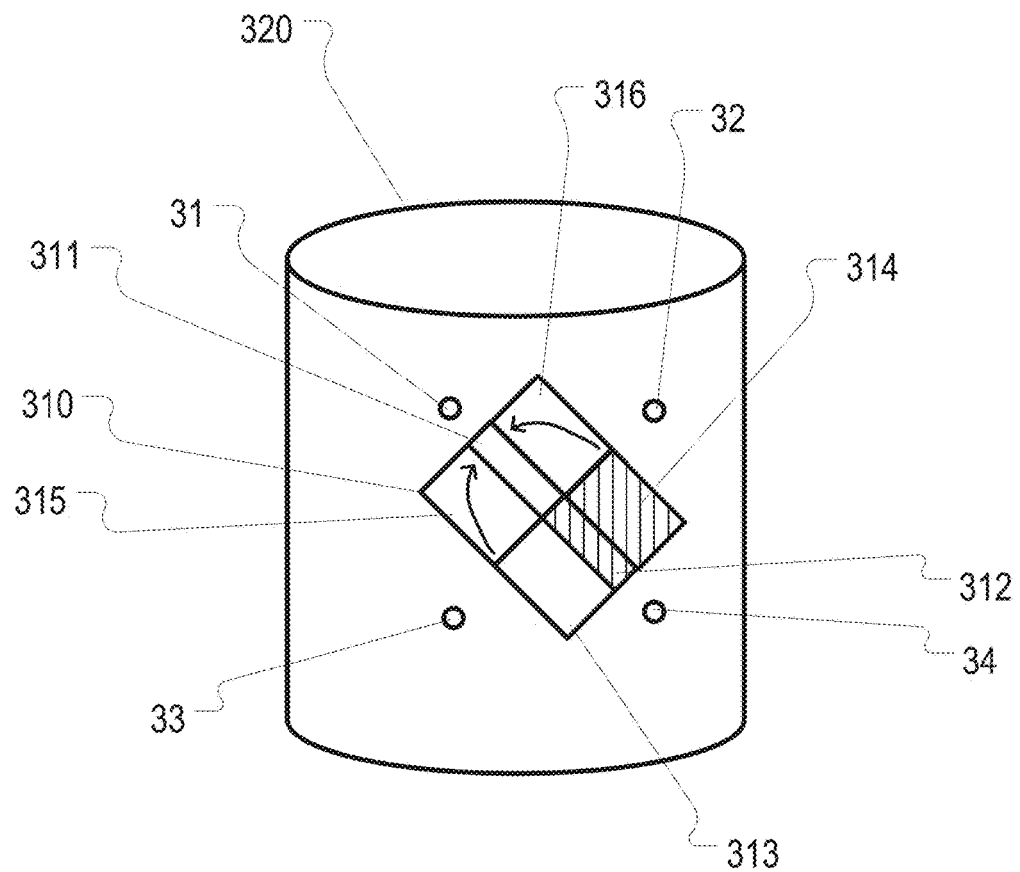

If the voltages are low or high in a particular region this can also suggest damage that is evident by electrical malfunction in that area. FIG. 13 illustrates an exemplary damaged electrically active structure 310 including components 311,312,313,314,315,316 lying in containing structure 320. The component 312 and the component 314 are damaged, as illustrated by the shading in the figure. Exemplary electrical current flow through each of the components 311,312,313,314,315,316 is illustrated in FIGS. 14A-D by arrows. Each of the figures schematically illustrates exemplary electrical flow from a first time point t1 to a next time point t2. FIG. 14A schematically illustrates exemplary electrical flow from time t=i to time t=ii; FIG. 14B schematically illustrates exemplary electrical flow from time t=ii to time t=iii; FIG. 14C schematically illustrates exemplary electrical flow from time t=iii to time t=iv; and FIG. 14D schematically illustrates exemplary electrical flow from time t=iv to a subsequent time point, which can once again be characterized as time t=i.

Figure 15:
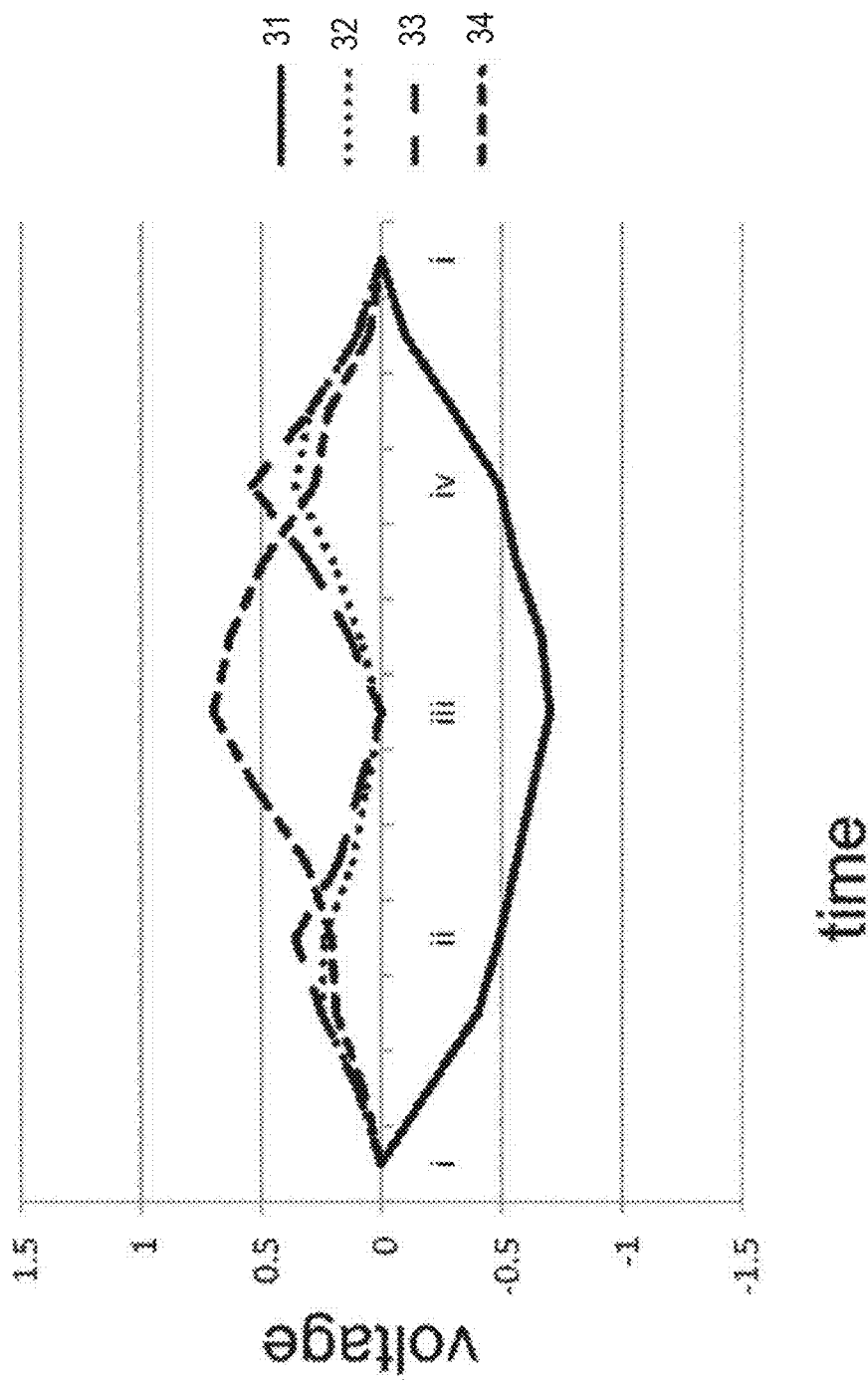
FIG. 15 illustrates a line graph depicting an active electric field produced by an electric current over time.
Figure 16:
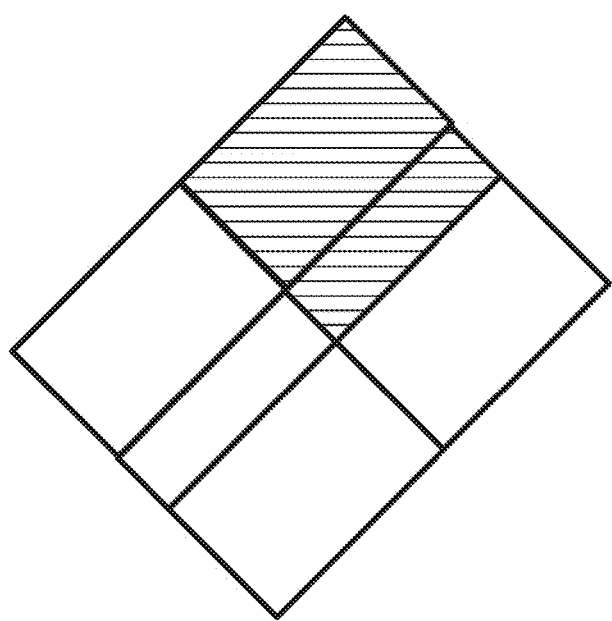
FIG. 16 illustrates a visualization of the electrically active structure of FIG. 13.
Figure 16:
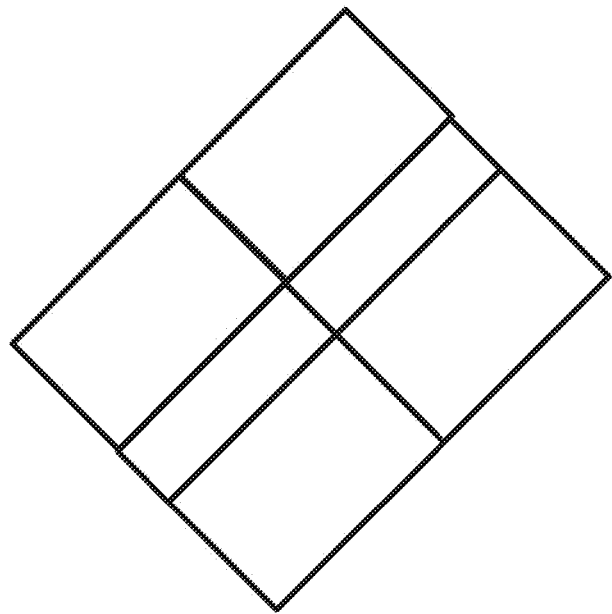

The damage, such as from a myocardial infarction, may interfere with the normal electrical transit through the structure 310 and can be visualized by mapping the voltage signals to a scalable graphic depiction. FIG. 15 illustrates a line graph depicting the active electric field produced by the electric current over time, and FIG. 16 depicts a visualization of the damaged electrically active structure 310 in a visualization space c compared to a normal electrically active structure 10. The damage is depicted in the figure via shading, although in alternative implementations such damage may be depicted in any number of ways. In some preferred implementations, overall size is visualized through the relative size of an electrically active structure within a containing structure, whereas damage, that will tend to have more of a focal change, such as from a myocardial infarction, could be represented in many ways such as by size, color, pixels, or brightness.

A normal reading can also be ascertained for an individual over time and a visualization could change if the normal voltage patterns for this individual changed, for instance during or after certain activities. An exemplary such use case involves monitoring and feedback during cardiac rehabilitation. If an individual exercised to the point where the heart was under too much strain, this could be represented graphically and such graphical representation would provide an indication to decrease the load to be in a healthier heart rate zone. FIG. 16 is an exemplary such depiction after mapping from physical space into sensor space into visualization space.

Figure 17:
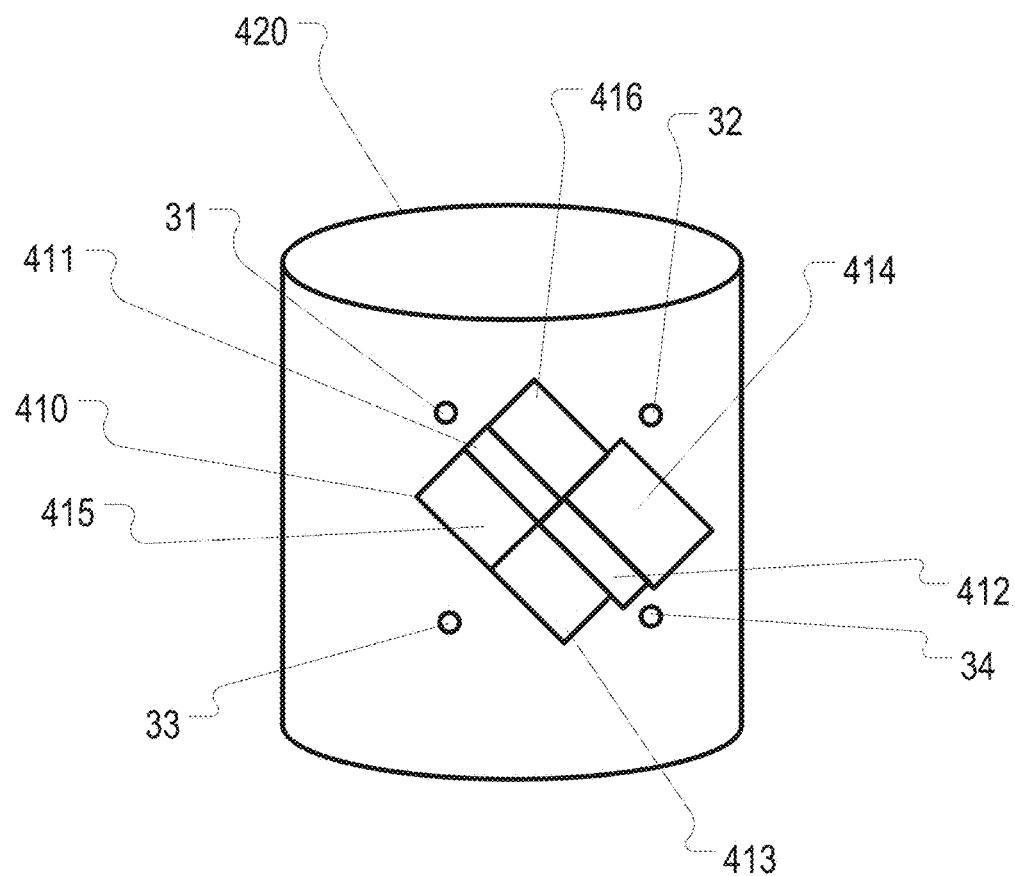
FIG. 17 schematically illustrates another exemplary electrically active structure.
Figure 18A:
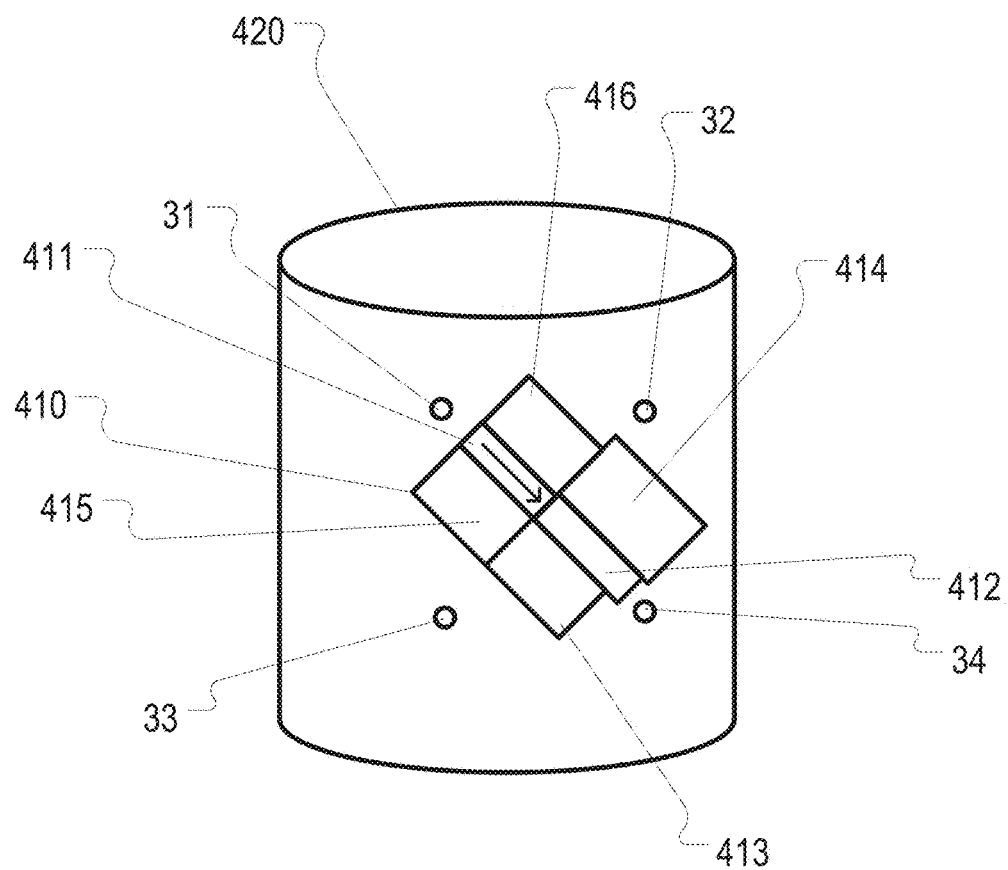
FIGS. 18A-D schematically illustrate electric current flow through the electrically active structure of FIG. 17.
Figure 18B:
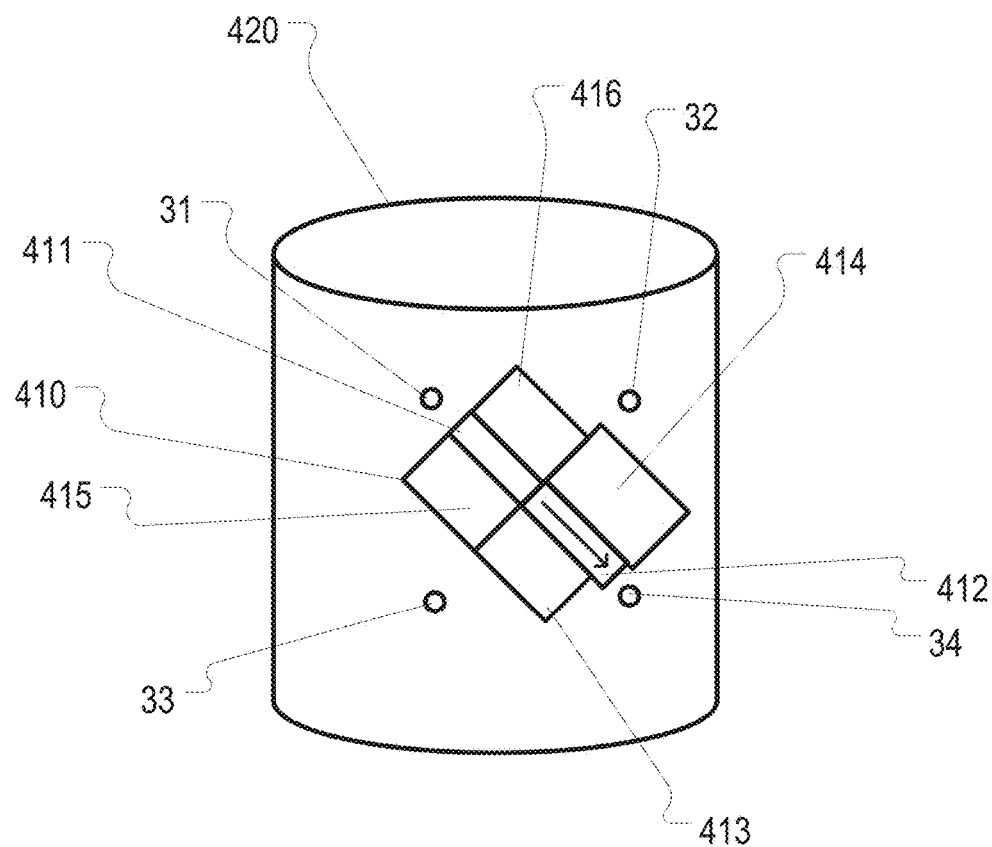
Figure 18C:
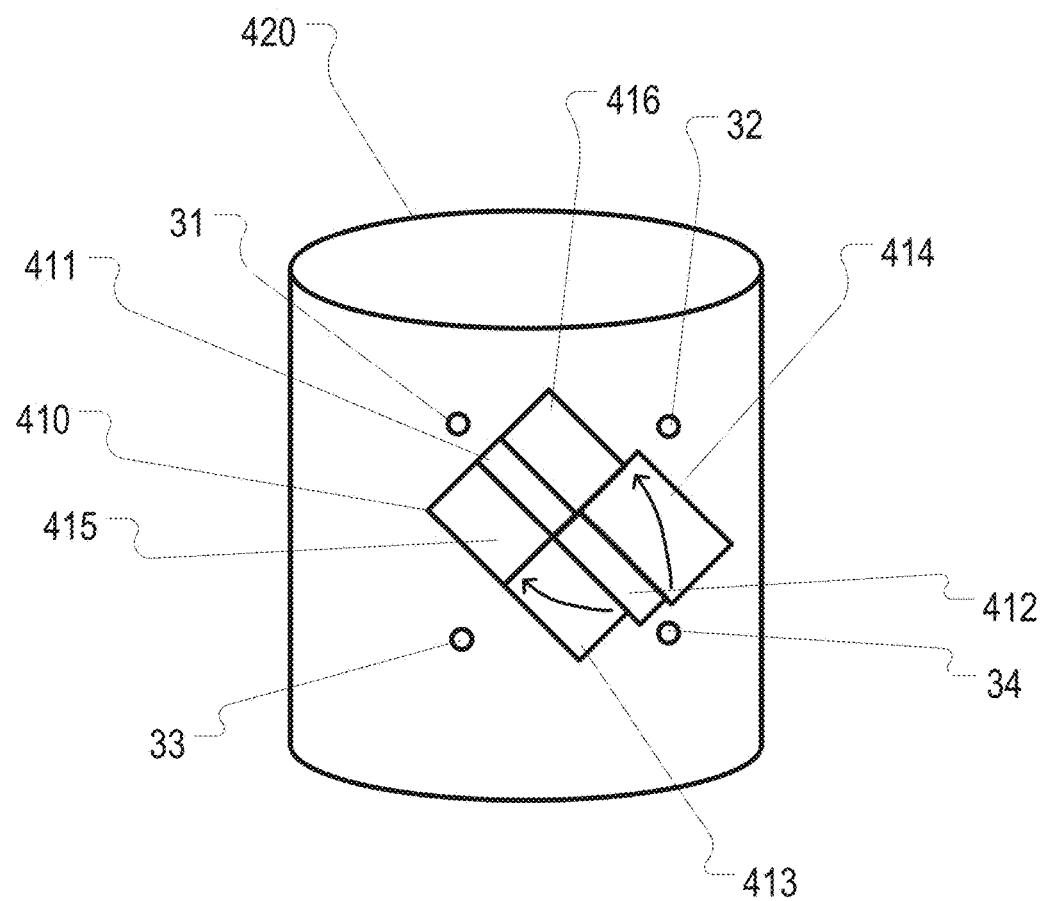
Figure 18D:
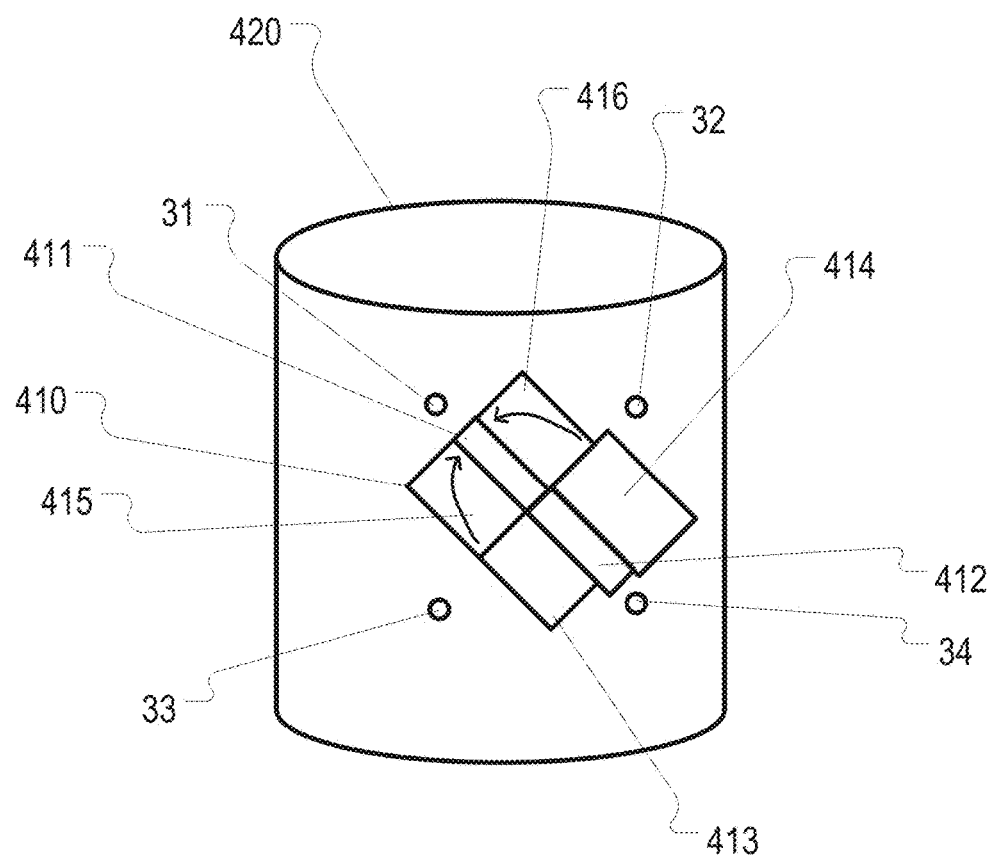
Figure 19:
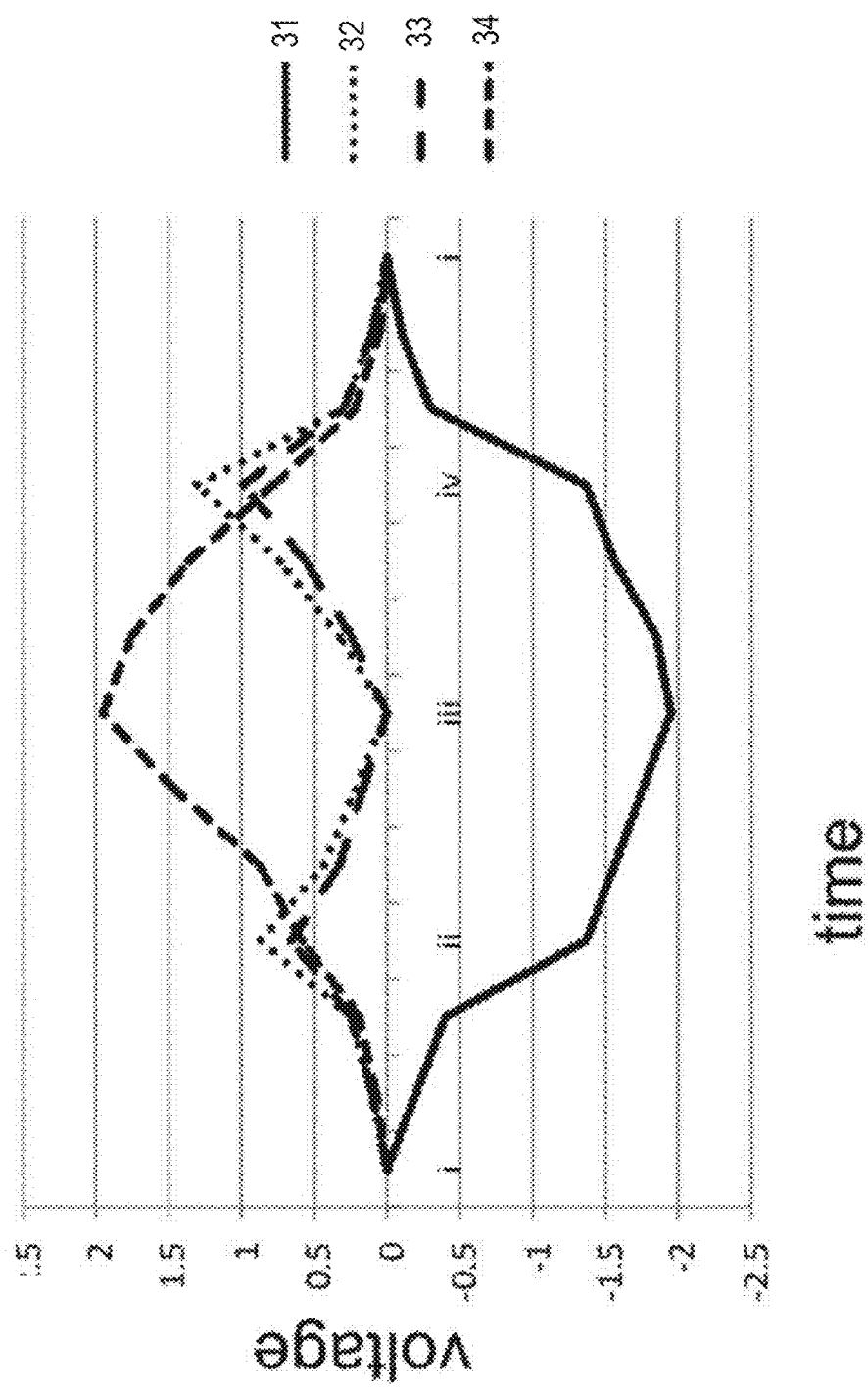
FIG. 19 illustrates a line graph depicting an active electric field produced by an electric current over time.
Figure 20:
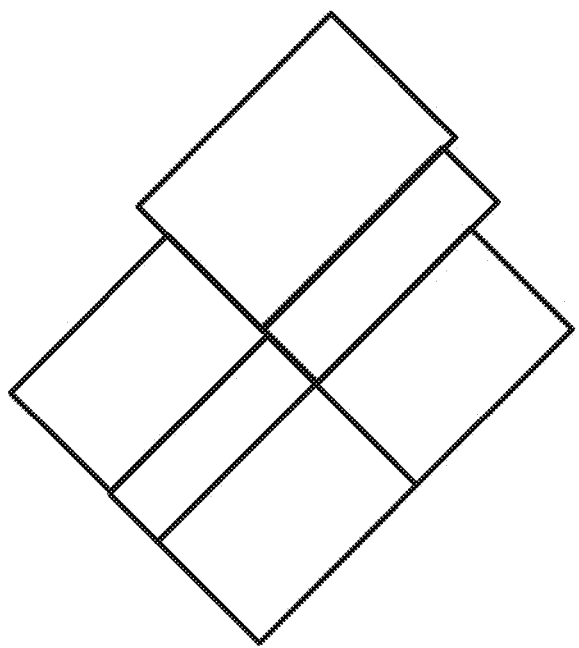
FIG. 20 illustrates a visualization of the electrically active structure of FIG. 17.
Figure 20:
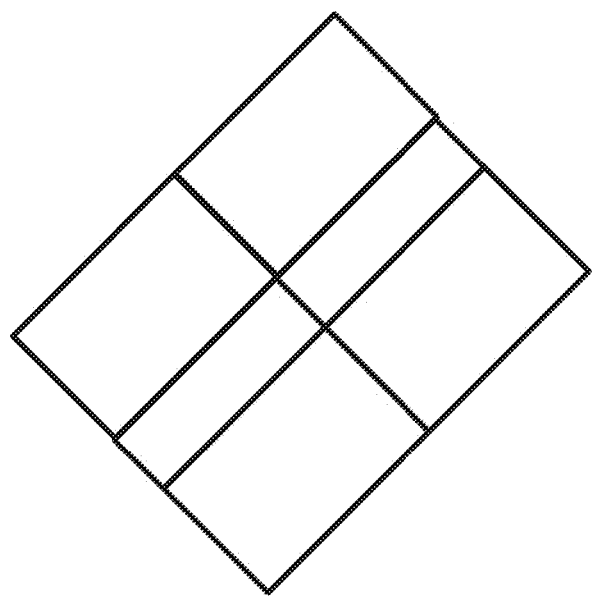

Another property that can be identified and visualized is that of shape change within a structure. FIG. 17 illustrates another exemplary electrically active structure 410 including components 411,412,413,414,415,416 lying in containing structure 420. Exemplary electrical current flow through each of the components 411,412,413,414,415,416 is illustrated in FIGS. 18A-D by arrows. Each of the figures schematically illustrates exemplary electrical flow from a first time point t1 to a next time point t2. FIG. 18A schematically illustrates exemplary electrical flow from time t=i to time t=ii; FIG. 18B schematically illustrates exemplary electrical flow from time t=ii to time t=iii; FIG. 18C schematically illustrates exemplary electrical flow from time t=iii to time t=iv; and FIG. 18D schematically illustrates exemplary electrical flow from time t=iv to a subsequent time point, which can once again be characterized as time t=i. FIG. 19 illustrates a line graph depicting the active electric field produced by the electric current over time, and FIG. 20 depicts a visualization of the smaller electrically active structure 410 in a visualization space c compared to a normal electrically active structure 10.

The electrically active structure 410 includes an increased area (which would represent increased volume in a three dimensional structure) of electrically active substance (tissue) in the component 412 and the component 414. This produces increased voltage deflection, especially in sensor 32, and that change in sensor space is transposed in visualization space as illustrated in FIG. 20.

Figure 21A:
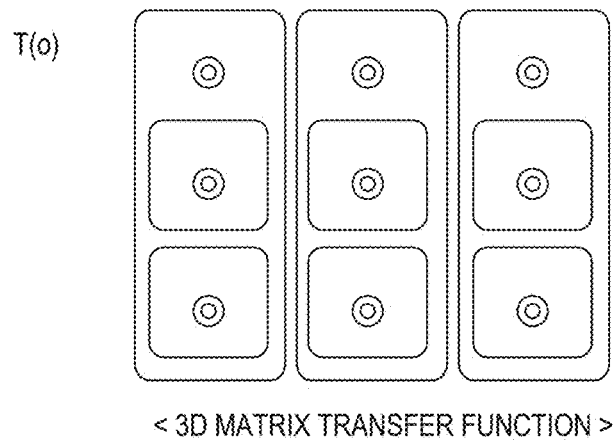
FIGS. 21A-B illustrate an exemplary graphical representation of a three-dimension electric field reconstruction over time (a fourth dimension)
Figure 21A:
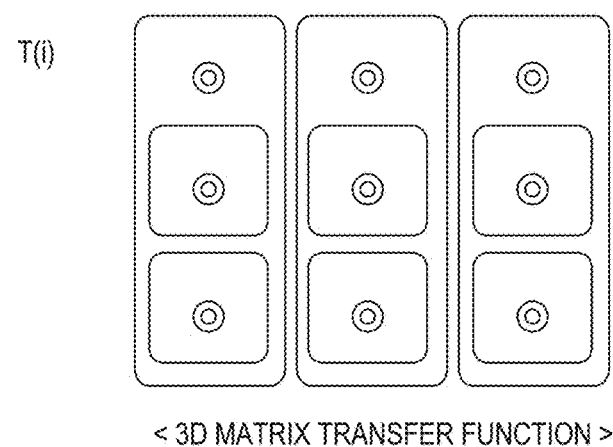
Figure 21A:
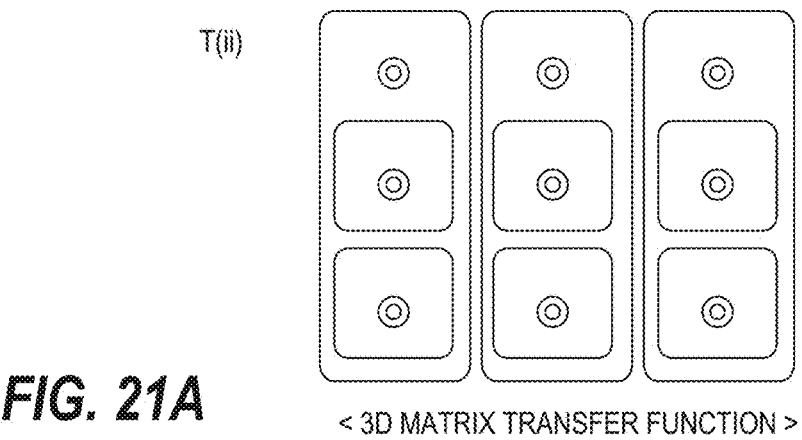
Figure 21B:
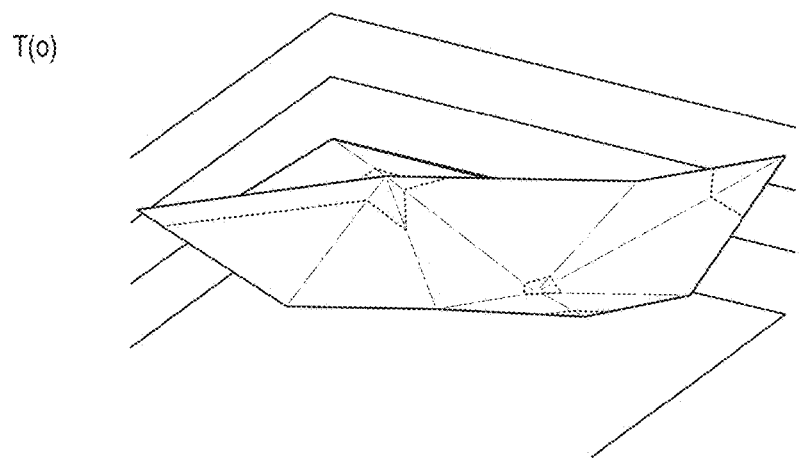
Figure 21B:
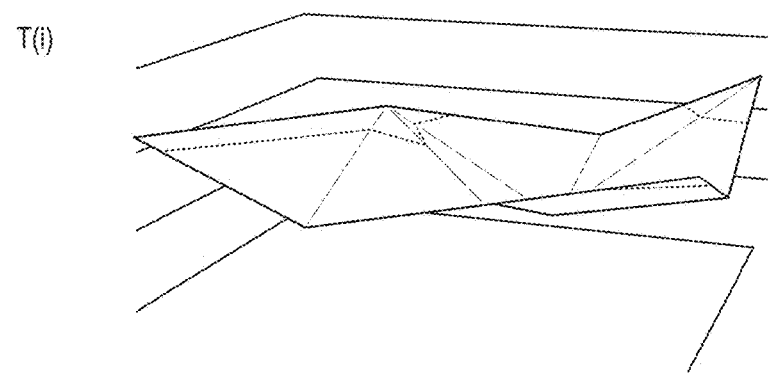
Figure 21B:
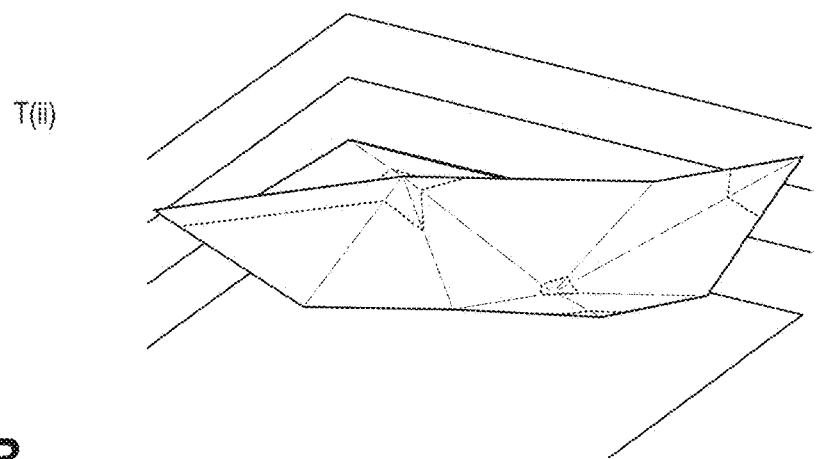

Although the illustrations thus far appear in two dimensions, one or more preferred implementations are implemented, and considered more useful in general, for use with objects in three dimensional space that have three dimensional electrical vectors running through them. FIGS. 21A-B illustrate an exemplary such visualization of a three dimensional object.

The majority of examples disclosed hereinabove refer to six components of an electrically active structure. With increased number and density of sensors comes higher resolution spatial information regarding the size and direction of vectors within a structure. In preferred implementations, this information is used to inform on the shape, size and electrical activity of a structure compared to a measured average over a population, or of a structure itself over time.

Different structures produce different signals. These signals can be decomposed from other signals through a variety of methodologies. Some exemplary such methodologies will now be described.

One or more of these exemplary methodologies relates to spatial proximity/amplitude. Electrical fields decrease in proportion to the square of the distance from the source. Therefore, the maximal electric signal that any structure will produce will be directly adjacent to it. For sensors further away, the signal will be reduced. This can inform on the position, shape and size of the object and through prior knowledge inform on the structure that is producing the signal. For example, the heart is in the left chest so the cardiac signal will be greatest over the left chest and will be detectable though significantly reduced in the abdomen, decreasing in amplitude as sensors are placed further away. Another example is the brain that lies in the skull. The electroencephalogram that is produced by brain activity is greatest in the head area and decreases further away. Therefore one method of identifying a signal is placing it over a known area and verifying the identification through progressive decay with distance from the source.

Figure 22:
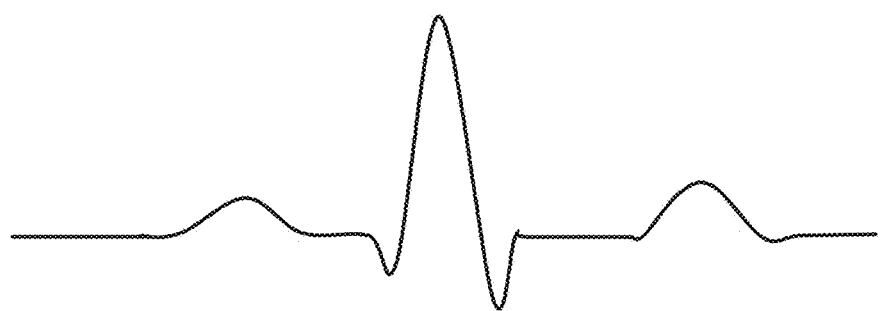
FIG. 22 illustrates a classic lead II cardiac electrical signature.

One or more other of these exemplary methodologies relate to shape. Electrical current flowing through different structures produces different shapes. The most well described electrical form is from the heart that produces an electrical signature (such as the classic lead II cardiac electrical signature that is illustrated in FIG. 22) that can be detected for the purpose of heart rate detection, beat-to-beat variability, and diagnosis of abnormal patterns or disease. Different sensors put on different regions around the heart referenced to different regions will produce a large variability in the electrical signature and can be used to interrogate the cumulative electrical dipoles as described herein.

Figure 23:
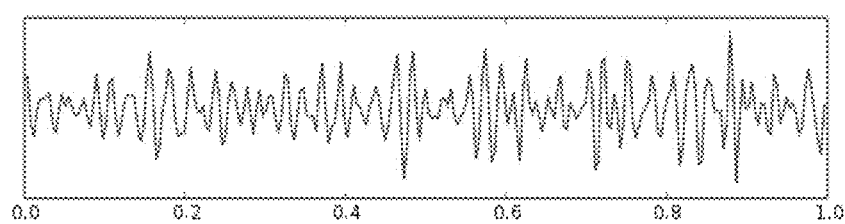
FIG. 23 illustrates a representation of a gamma wave measured over 1 second.

One or more other of these exemplary methodologies relates to frequency. Some structures, such as the brain, produce a voltage time trace that is composed of many different shapes and amplitude waveforms. This can be problematic for signal deconvolution, and one method to isolate different waveforms that may correspond to structures or shapes is to perform frequency analysis. The "state" of the brain or components of the brain for instance can be represented by the relative power of different frequencies of brain voltage/time relations. By applying frequency subtractions (bandwidth filters), the voltage/time signal can then be deconvoluted, and the shape of the wave forms identified (as illustrated in FIG. 23, which represents a gamma wave measured over 1 second).

For the brain, the wave forms fall into the following frequency silos with associated classical functional conclusions:

Delta waves (0.5-4 Hz), identified with deep dreamless sleep or transcendental meditation;

Theta waves (4-7.5 Hz), identified with deep meditation, light sleep;

Alpha waves (7.5-12 Hz), identified with deep relaxation, daydreaming, light meditation;

Beta waves (12-30 Hz), identified with normal waking, also higher alertness, logic and critical reasoning. Higher beta frequencies can indicate into stress or anxiety; and Gamma waves (25-100 Hz, but usually ~40 Hz), generally thought to be identified with short bursts of insight, or with high level information processing.

One or more other exemplary methodologies relate to use of known path information. In structures such as the heart and muscles, there are known normal paths for electrical signals that makes structural reconstruction from an electrical signal relatively direct. Any deviation from this path in a structure that has already been mapped provides direct information on either the structure or the function of the tissue, e.g. as described herein. This is primarily due to the structure of these tissues that limits the angular, and to an extent magnitude, freedom of variation for individual and grouped electrical dipoles. In the brain, however, this situation is not so well defined as there exist multiple dipoles. One method to ascertain the structural and functional integrity and subsequent visualization of the brain is to use external stimulation that follows a known path through the brain. For instance, the visual evoked potential follows a predictable path and timing through the optic nerve, crossing at the optic chiasma and activating the contralateral occipital cortex. Therefore, sensitive electric field sensors that were along this path would be able detect the integrity of this path when synchronized with the visual stimulus. The same can be done for other sensory, cognitive and motor inputs including, but not limited to: muscle reflexes, motor instructions, auditory inputs, and tactile inputs. To further identify these inputs, they can be frequency tagged so the path of different frequencies and harmonics of these frequencies can be tracked through the brain, informing of the electrical, functional and structural integrity of the brain. Repeated measuring of the response to a stimulus allows removal of random noise by averaging the results, and provides a much clearer signal than a single EEG reading.

One or more other exemplary methodologies relate to increasing spatial fidelity. By increasing the number of sensors in a sensor array, better spatial resolution can be achieved. With particular reference to electric field sensors, the spatial resolution is enhanced over conventional resistive contact electrodes as the sensors do not draw any significant current from the source leading to more effective mapping reconstruction for visualization as they do not interfere with the source or other sensors around them. Unlike resistive contact sensors, electric field sensors are also resistant to sweat and shorting between electrodes. These qualities allow for higher density arrays and can be utilized, for example, with methodologies described herein so as to effect visualization of the electrical signals moving through objects.

One or more other exemplary methodologies relate to using other interrogation modalities to inform, target, calibrate, and validate the electric field visualization in populations or individuals.

Further, in one or more preferred implementations, other scanning modalities such as functional magnetic resonance imaging (fMRI) or spectroscopy are utilized to identify electrical firing patterns.

For example, in an exemplary use case related to brain interrogation, there may be an increase in electrical activity, however, the dipoles may not be at the appropriate vector position for direct over structure pick-up. Therefore, sensor position may need to be changed to pick up the increased activity based on other imaging methods.

In another exemplary use case, sensor findings may be verified or tuned by either ultrasound or X-ray when visualizing the structure of an electrically active object such as one or more muscles or the heart. This type of validation could also be used for other structures, such as, for example, the lungs, gastrointestinal tract, or blood vessels.

In one or more preferred implementations, accelerometers incorporated within or close to the sensors could detect movement that may relate to either artifact of muscle movement, thereby validating any electromyogram (EMG) activity detected.

In one or more preferred implementations, systems and methods for brain visualization are provided. Brain waves are fairly uniformly periodic, and can be classified by identifying the characteristic frequency. Fourier analysis lends itself readily to the analysis and separation of these different waves. As the different frequencies of brain waves correspond to different states of consciousness, in one or more preferred implementations, brain waves are visualized by assigning a different color to each type of wave. For example, in an exemplary implementation waves associated with stress and anxiety are displayed in red, alert states in yellow, deep relaxation in blue, etc. In a preferred implementation, a figure of a body is generated with an "aura" of the colors associated with each brain wave drawn around it. The thickness of each color in the aura is in proportion to the amplitude of each type of wave in the spectrum, and thus the aura of a very stressed and anxious person would appear mainly red for example, and that of a person deeply asleep would be mainly blue. The set of brain waves detected can be represented as a set of simple sinusoidal waves with appropriate periods.

In one or more preferred implementations, systems and methods for visualization for structures other than the heart, brain and muscles are utilized. For example, such visualization may comprise visualization of the lungs. The main electrical signature the lungs will create is through changing impedance and displacement of electrically active tissue and the active movement of the diaphragm muscle. The electrical signal produced by blood vessels will be through the electromagnetic charge associated with flow of low impedance and ferrous fluid through relatively high impedance walls and surrounding tissues. The signature from the gastrointestinal tract will be a mixture of high impedance areas due to gas build-up, electrical activity from smooth muscles, and general movement of the intestines displacing electric fields.

A non-resistive contact electrical potential sensor may be used in combination with other non-perturbative or perturbative sensors. In some implementations, information from such sensors is assembled and incorporated into a visualization model for data representation. Any combination or permutation of sensor types can be used to obtain an optimal visualization.

Exemplary such non-perturbative sensors and sensing methodologies include: Passive Sonar; Magnetometers; Cameras—whole spectrum from IR to UV; and Thermometers and Hydrometers. Exemplary such active and perturbative sensors and sensing methodologies include: Active Sonar; X-ray and computerized tomography (CT); Radar; Impedance tomography; Magnetic resonance imaging (MRI); Resistive contact electrometers; Nuclear medicine scanners; Spectroscopy; Angiography and fluoroscopy. Each of these exemplary sensors and sensing methodologies will now be described in more detail.

In one or more preferred implementations, a sonar sensor or sensors is utilized for interrogation of the physical structure, shape, and form of an entity or entities by either passive or active methods. They may be used to locate and determine the characteristics of a structure and its reference point(s) relationship(s) to electric field sensor(s) placement. This can be used for more accurate placement and/or more accurate identification of the electric field signal source(s) and hence useful data that will lead to more accurate metrics and may act as an aid to spatial reconstruction.

The signal transduction for a sonar device or devices can occur at either the surface or internal layer of the entity or at a distance from the entity.

Sonar sensors can inform on physical shape and distance plus the electric field sensor informs on electric or magnetic characteristics and distance. By combining the sensors synergistic and cross-validating information is obtained adding a new level of functionality. Preferably, thereby, more effective structural and functional imaging reconstruction is achieved.

Active sonar modalities such as ultrasound have effectively been used to elucidate the structure and functional characteristics of entities. Ultrasound modes such as Doppler allow a practitioner to assess blood or fluid flow within an entity. In some preferred implementations, this data, in combination with other data sets such as that gained from non-resistive contact electrometers, is overlaid and visualized to provide further useful information about the state of an entity or entities.

Additional disclosure of sensors, systems, and methodologies that may be utilized in one or more implementations is included in U.S. patent application Ser. No. 13/527,862, which is hereby incorporated herein by reference.

In one or more preferred implementations, one or more magnetometers, such as, for example, atomic magnetometers, Hall magnetometers, Spin-Exchange Relaxation-Free (SERF) magnetometers, and Superconducting Quantum Interference Device (SQUID) magnetometers, are utilized.

The data from magnetometers is preferably utilized to effectively gain useful physiological data. In some preferred implementations, the combination of this data with the data from electric field sensors is integrated to provide a visualization of such data.

Cameras capture visual data so are well placed for visual representation. In some preferred implementations, the combination of this data with other sensor data including that obtained from non-resistive contact electrometers provides additional useful data.

Thermometers can be used to track the temperature inside and on the surface of an entity or entities. In one or more preferred implementations, this data is overlaid with other data and visualized to provide further useful information about the state of the entity or entities.

Hydrometers can be used to track the water content within or on the surface of an entity or entities. In one or more preferred implementations, this data is overlaid with other data and visualized to provide further useful information about the state of an entity or entities.

X-rays and computerized tomography are effective processes to visualize anatomical data. In one or more preferred implementations, combination of one or both of these processes and their subsequent acquired data with non-resistive contact electrometers in an integrated visualization provides additional and synergistic structural and functional information.

Impedance tomography can be used for mapping of entities. In one or more preferred implementations, impedance tomography data, utilizing non-resistive contact or resistive contact electrometers, is overlaid and visualized with or without other datasets to provide further useful information about the state of the entity or entities.

Radar, such as ultra wide band radar has been successfully used to interrogate the internal structure and functioning of entities such as the heart. Combining radar signature with electric field data will further inform on the structure and function of an entity such as the heart.

Non-resistive contact electrometers have been successful in picking up magnetic resonance signals, as have magnetometers. MRI scanning is well established as a method to acquire and visualize structural and anatomical data. In one or more preferred implementations, this data, in combination with other data sets such as that gained from non-resistive contact electrometers, is overlaid and visualized to provide further useful information about the state of an entity or entities.

Resistive contact electrometers can be used to gain a level of understanding about the electrical state of an entity. For example, combinations of chest leads in a traditional EKG exhibiting characteristic signatures can assist in the diagnoses of infarction, or altered electrical flow, in a general region of the heart. Though the accuracy of such diagnoses may be flawed due to the draw of current, this data may also have use in combination with non-resistive contact electrometers. In one or more preferred implementations, this combined data is overlaid and visualized to provide further useful information about the state of an entity or entities.

The utilization of radioisotopes to provide useful information about an entity is well established and nuclear medicine scanners are used in wide practice in hospital facilities. In one or more preferred implementations, a combination of the data obtained from nuclear medicine scanning, with other data sets such as that gained from non-resistive contact electrometers, is overlaid and visualized to provide further useful information about the state of an entity or entities.

Spectroscopy is widely used in medicine for the elucidation of functions such as blood flow. Near infra-red spectroscopy is, for example, used to assess the intra-cerebral blood and combining this with electric field data from the heart and brain would further inform on the structure and function of the brain and its vascular supply.

Angiography and fluoroscopy through injection of contrast agents provides useful information about the structure of vessels and other lumens with an entity. In one or more preferred implementations, a combination of the data obtained from angiography and fluoroscopy, with other data sets such as that gained from non-resistive contact electrometers, is overlaid and visualized to provide further useful information about the state of an entity or entities.

Using systems and methods described herein (and in the incorporated reference), different structures can be visualized based on, for example, sensor proximity, signal shape, frequency, amplitude, and relation to other imaging/detection modalities. With multiple sensors, different systems can be visualized in a manner that visualizes the relation amongst them. To add further value, imaging from other modalities such as x-ray, MRI, CT, conductive electrodes, spectroscopy, ultra-wide band radar can be overlaid to provide a broad overview of the functioning of the body at the current time, which can be compared with historical recordings for monitoring purposes. Visualization methodologies described herein are believed to provide the tools to identify how different signals combine to inform the overall health/state of a person.

As an electrically active component such as skeletal or cardiac muscle moves, the electrical vectors within it will also move in space. Therefore, the movement can be tracked by analyzing the change in electric field as it runs through the anatomical structure of the component. This can then be visualized as both an electrical and mechanical output. The analyses and visualization can be further refined by taking into account background knowledge of the physiological relationships of electrical and mechanical activity in structures. An example of this is the electrical activity flowing through the heart preceding the mechanical contraction of the cardiac chambers. Using methodologies discussed herein, a dynamic visualisation of the body can be produced showing a heart beating in time with a subject's pulse. The various chambers of the heart may be more or less brightly lit depending on the measurement of the electrical axis. Concurrently, the activity of the brain at the time could be represented visually by shading, colour or other representative graphics. Other parts of the body could be similarly depicted and visualized concurrently as well.

In systems and methods in accordance with some preferred implementations, the sensors and sensor types are not necessarily tethered spatially or temporally. For example, an ultrasound probe may be used to identify a structure for the best placement of electric field sensors. The placement area is marked and the ultrasound probe is withdrawn. The sensors are then placed on the placement area and data is collected. In this use case the sonar and electric field sensor are not tethered in time or space.

For invasive procedures or implants, a sensor can be enveloped in a biocompatible sleeve that allows for reuse of the sensor (e.g., a single sensor can be used multiple times). Use of the sleeve allows a completely biocompatible shield to be placed around the sensor. The sleeve can be disposed ensuring sterility of procedures.

Preferably, methodologies described herein (such as, for example, use of a sleeve representing a completely biocompatible shield) allow for measuring with minimal interference with a signal being measured. That is, preferably, such methodologies (and the accompanying technology utilized therefore) are non-perturbative. This preferably provides an advantage in that sensors do not interfere with a target signal allowing more effective structural and functional signal reconstruction.

In one or more preferred implementations, sensors are used in a mobile scanning mode and/or separate sensors are arranged in arrays, a structural and/or functional construct of underlying structures can be made. By using sensors in a mobile scanning mode or arranging the separate sensors in arrays, a structural and/or functional construct of underlying structures can be made. Further, by linking three-dimensional images over time a four-dimensional image can be created (in accordance with one or more preferred implementations), with the time continuum representing the fourth dimension.

In accordance with preferred implementations, sensors can be tuned and selectively guarded to pick up a variety of physiological signals across the electric and magnetic spectrum. This tuning can be done either with sensor hardware, or digitally after an analog signal has been converted to digital. In some preferred implementations, for this purpose, a system can detect many electric and magnetic field signals, including nervous, muscle and other electrical conduction, fluid flow, and structural determination above and beyond, and without the limitations of, and in combination with, other state-of-art imaging technologies.

In accordance with preferred implementations, a variety of visualization methods may be used including but not limited to the use of fixed or variable shapes, colors, two-dimension displays, three-dimension displays, sound, texture, heat, and holograms. Such visualizations may be represented statically or as change over time as in video representations.

FIG. 21 is an exemplary graphical representation of a three-dimension electric field reconstruction over time (fourth dimension). In this case, a sensor array is placed over a region of the body. Signals are collected at three time points [T(o), T(i), T(ii)]. The nine signals are processed through a three-dimensional matrix transfer function to create an image reconstruction of an electric field at the three different time points, as illustrated in FIG. 21.

In accordance with one aspect of the invention, a sensing apparatus for use with an entity includes a housing and a sonar transducer within the housing and is adapted to detect a signal generated by an entity. Preferably, the sensor includes at least one sensor adapted to detect an electric field or fields associated with the geoelectric displacement signature or structures of the entity.

Heart sounds can be correlated with electrical activity of myocardium which can be assessed through clothing, wound dressings and so forth. In some preferred implementations, an electric field detector is used where electric potentials can be measured through clothing and/or wound dressings and/or fur and/or any other impediment to resistive contact and usefully combined with acoustic or ultrasound signals to provide valuable information about the status of an individual, animal or a non-biological entity.

In accordance with another aspect of the invention, a sonar sensor is used to identify and characterize a target structure and any other structures that may interfere with the electric or magnetic field. The electric field sensor is used to characterize the electric or magnetic field properties of the target and other structures. The sensors may be physically coupled or separate.

In accordance with another aspect of the invention, a sonar system could be used to assess respiratory and heart sounds while the electric field sensors detected the electrical signature associated with breathing and the heart. This could be visualized to inform on a subject's cardiorespiratory status. The use cases for this range from monitoring human performance through to monitoring and detection of disease states.

The combined sensors can be used for visualization and location of a nerve for accurate acquisition of electric potential signature. In a preferred implementation, an ultrasonic, MRI, x-ray or other imaging device images the nerve, using known and established principles of medical practice, determining the best anatomic location for non-resistive contact electric field sensor placement. This determines the distance from the target and also the characteristics of tissue overlying the target. The breadth of adipose tissue, that has higher electrical impedance, is determined. In preferred implementations, for optimal placement, sensors are placed in an area where the nerve is closest to the surface and, ideally, each electric field sensor. Furthermore, sensor placement ideally occurs at a place where the adipose tissue is minimal and close to the same thickness at different sensor locations. This information helps aids in interpretation of the electric field signal and also the placement of the electric field sensors. The electric field signal output is a voltammetric signature recorded as the difference between the recording and the reference electrode(s) where the reference electrodes would generally be orthogonal to both recording electrodes. Using this approach, the nerve conduction velocity would be best obtained. In some preferred implementations, a target voltammetric signature is determined by subtracting known noise and by restricting bandwidth to known frequencies of the signal of interest. In some implementations, another sensor type can be utilized during this phase for the detection of muscle movement aiding the subtraction of the muscle noise component of the signal.

In some preferred implementations, studies comparing normal individuals to those with known nerve conduction problems are performed and/or utilized so patterns of nerve damage using this new technique can be recognized. This approach is believed to be advantageous for the diagnosis of nerve damage or compromise by comparison to normal neural signal activity in control populations. Currently, nerve damage is typically diagnosed with invasive fine needle nerve conduction studies. Some preferred implementations allow for non-perturbative diagnosis saving considerable time, money and preventing negative side effects associated with invasive studies.

Another advantage would be for compartment pressure testing where nerves may be compromised through high internal compartment pressures. In a preferred implementation, diagnosis of this is effected by comparing a normal population with individuals with the known condition. Preferably, pattern analysis and comparison of the data results in pattern identification leading to pattern recognition software developed especially for this purpose.

Currently, diagnosis of high compartment pressures involves invasive procedures where a catheter is inserted into the compartment and the pressure is read through a pressure transducer. In some preferred implementations, systems and methods in accordance with the description herein are utilized in lieu of conventional technology as a diagnostic device.

Such systems and methods, especially in implementations utilizing implantation, could also be used to record neural output to control a prosthetic or other device as when a nerve has been severed or there is the desire to control a distant machine for any reason. The technology could also be used for recording the neural output from the autonomic nervous system for diagnosis, monitoring and treatment of a variety of conditions including emotional stress, depression, post traumatic stress disorder, epilepsy. For biofeedback, this technology could be used to optimize performance through feedback control of autonomic outputs.

Another embodiment is for the structural and functional visualization of muscle using the electric field and sonar sensors—cardiac, skeletal or smooth muscle may be visualized and correlation with movement and electrical and magnetic activity can be made. This is useful for investigating correlations between structural and neural muscle damage. It is entirely non-invasive and provides information that may help diagnose and monitor a variety of conditions including infarction of the bowel, myocardial infarction, muscle trauma, muscular dystrophies and neurodegenerative conditions. As described hereinabove, this may also be able to be used for diagnosis of compartment syndrome. With high compartmental pressure, muscles become starved of oxygen and that will change the electrical signature. Therefore the change in electric signature may be used to diagnose the characteristic decrease in perfusion of muscles that occurs with compartment syndrome, replacing the need for invasive compartment pressure testing.

One or more preferred implementations are preferably used to image fluid flowing through a vessel, such as for biological purposes, though it could also be used for non-biological purposes, such as for identification of underground fluid reserves or for rivers. Sonar, X-ray, radar, computerized tomography, magnetometers, and MRI modalities can be used to pick up characteristics of fluids and vessel walls. Non-resistive contact electric field sensing can also be used as fluids, especially when flowing through a material that differs in impedance to the fluid, generate an electromagnetic signature. A electric field sensor may be used to pick this up. This has use for diagnosing and monitoring blood flow, and may be useful for triaging of casualties, or monitoring vessel blockage and/or compromise. This may replace current technologies, many of which are invasive or impractical for other reasons, such as, for example, a need for expert operation, being immobile, or expense.

In one or more preferred implementations, a more complex methodology combines structural, electrical and fluid dynamic information for more complete imaging. Such signature acquisition of the various structures can be accomplished in accordance with description herein. Put together, a preferred implementation may inform on the electrical activity of an organ, the structural integrity and movement of muscle, and the outflow from the organ itself. Such combined technology preferably provides a high level of clinical information and may inform on diagnosis, effect of treatment, and progression of disease. This same application can be made to a variety of organs within the body including but not limited to the: heart, lungs, liver, kidneys, bladder, skin, spleen, pancreas and bowel.

Non-resistive contact electric field sensors may also inform on the structure and function of the central spinal cord and of the brain.

In accordance with another preferred implementation, a sensor assembly for use with an entity may include a series of sensors, being a combination of at least one sonar sensor with electric field sensors for the monitoring of an entity or entities.

In one or more preferred implementations, a sensor system is used for monitoring of people or other entities in a room. People may be identified and tracked from their visual, sonar, magnetic or electric field signature. In the case of their sonar signature it may be actively determined from their shape or passively determined by characteristic features including voice, breathing and gait recognition. Their electric field signature may be identified through geoelectric displacement information including reconstruction of shape and movement or characteristic electric field information such as the pattern and amplitude of their cardiac or respiratory characteristics. This technology could be used with a variety of other sensors or sensor systems informing other identifications such as use with visual recognition systems. This is useful as an electric field sensor can sense remotely so could be used to track people through walls or underground. It could also be used to identify machinery and track it. This would be especially useful for equipment that has a strong electromagnetic presence including communications equipment.

In accordance with some preferred implementations, one or more electric field sensors are combined with active technologies including tomographic techniques where an electric field is passed through an entity and the output at the other end is characterized by the electric field sensor or sensors.

In accordance with some preferred implementations, a sonar component is used to detect sounds emitted from an organism such as breathing or talking. Such use may be either alone or in combination with non-resistive contact electric field sensors or other sensor technologies for the diagnosis or monitoring of medical conditions including sleep apnea, heart failure, pneumonia, or hemothorax. The diagnosis of heart failure, for example, may be aided by an altered resonant frequency in the bases of the lungs as vocal and/or breath sounds move through fluid, in combination with a change in the electric potential signature from the myocardium.

In one or more preferred implementations, technology and methodologies described herein are incorporated into a mobile phone or similar device.

In accordance with one or more preferred implementations, sensors are combined with a magnetometer or magnetometers to provide additional information about an entity. A combination electric field sensor and magnetometer would be useful as such an implementation would provide information about power usage of certain structures as power is a function of voltage, as measured by an electric field sensor, and current, as measured by a magnetometer. In this case, a sonar sensor or sensors could be further used to provide information about the structure of the device or related objects and relate it to effects on power usage.

With respect to at least some implementations, there may be no need for combination sensor components, once developed.

One or more preferred implementations are preferably usable for real time and post-processing: peripheral and central nervous system assessment and/or mapping/imaging; skeletal, smooth and cardiac muscle electrical and functional assessment and/or mapping/imaging; bodily fluid and solid structure assessment and/or mapping/imaging; structure functionality measurement; and structural composition assessment.

One or more preferred implementations preferably provide the following functionality:

Measurement of important functional physiological data; potential for high resolution structural image sequences; potential for high resolution functional image sequences; a relatively cheap technology compared with current imaging techniques; relatively easy tailoring to meet specific needs; potential for high portability; use with mobile phone technologies; use for assessment of cognitive status; lack of need for extensive shielding; lack of need for special operating conditions; a passive sensing technology that does not interfere with underlying physiological signals allowing for more accurate reconstructive imaging; enhanced recording of deep electrical activity; structural, and electrical signal change signals over time, and the correlations between these signals; obviation of need for electrical contact; obviation of need for skin preparation or conducting pads; ability to read signal through wound dressings and/or clothing; ability to be readily moved to get optimal signal; ability to miniaturized; very low power requirements; use when the skin integrity is compromised; sensor functionality for sterile procedures; remote monitoring; electrical safety; decreased potential preparation time; synergistic source information; obviation of need for data to be collected at the surface of an entity; avoidance of invasive procedures; reusability; use of a combination of sensors to enhance the ability to identify, locate and track entities; ability to gain synergistic information about an entity; increase of information for diagnoses; increase of information to allow biological, structural, and functional imaging.

An exemplary use case involves early assessment of cardiac muscle death post Myocardial Infarction (MI). Traditional EKG diagnosis gives a rough indication of infarct size, progression and treatment efficacy post MI. This is, however, limited by both the active nature of data acquisition, that is, current is drawn from the source, and also traditional placement of leads. One approach is to treat the thorax as a series of different sized cylinders and account for underlying structures such as the lungs and adipose tissue. By doing this a three dimensional representation of electrically active myocardium can be assimilated. Variation in electrical activity in different regions can be mapped to allow assessment of cardiac muscle death, stress and health. Utilization of this information may allow more efficient targeting of resources and more accurate assessment of treatment efficacy.

Another exemplary use case relates to direct measurement of Autonomic Nervous System (ANS) function. The ANS is the neural controller of all unconscious bodily functions. Measurement of autonomic function has particular clinical interest as it may give an indication of: short and long term prognosis in a variety of disease states; mental and physical stress states; likelihood of having an epileptic seizure in the short-term; risk of sudden cardiac death; over-training; and capacity for physical or mental performance.

The current state of the art measurements of ANS function involve measurement and interpretation of the secondary effects of the autonomic nervous system (for example: sweat response, heart rate variability, drug challenge) or direct invasive microneurography (insertion of needle electrodes into the peroneal nerve to measure sympathetic outflow).

By placing arrays of passive electric field sensors over autonomic nerves and subtracting background noise, by using analog and digital extraction techniques, such as bandwidth limitation algorithms, produced from sources such as skeletal and cardiac muscle activity, a relatively pure neural signal can be obtained. The signal can then be constructed in three dimensions and mapped to known neural pathways to differentiate the signal from other nerve types such as those controlling skeletal muscle activity. Using this method, autonomic function can be directly measured providing clinically useful information with applications as outlined herein.

Another exemplary use case relates to non-invasive nerve conduction studies. To determine neural function, the current state of the art is to insert needle electrodes directly into nerves for measurement of current. This invasive procedure has limitations in that: it requires specialist premises and personnel; it is inconvenient and uncomfortable; insertion of needles almost certainly interferes with the neural signal; and, to locate a lesion, multiple measurements along the length of a nerve are needed.

By using passive electric field sensor arrays, and three dimensional reconstruction techniques, as discussed herein, neural activity can be assessed non-invasively and simultaneously along the entire length of the neural structure allowing both assessment of function and location of any potential lesion.

Another exemplary use case relates to measurement of cardiac output and vascular function. Assessment of cardiac output is a mainstay of emergency and critical care medicine. There are a variety of basic and advanced clinical techniques available ranging from: simple palpation of a pulse, to the sphygmomanometer, to echocardiograms, to dynamic magnetic resonance imaging, to invasive dilutional cardiac catheterization.

Any flowing fluid creates a relative electromagnetic field in relation to its surroundings. Quantification of this electromagnetic field utilizing arrays of electric field sensors and reconstruction of the raw data into four dimensions allows assessment of cardiac output. On a more regional level this technique can be applied to specific blood vessels such as the femoral artery for the accurate diagnosis and location of peripheral vascular disease.

Another exemplary use case relates to whole body imaging. By using arrays of passive electric field sensors, the whole body can be imaged. Variations in sensor sub-type and three-dimensional reconstruction combining electric and magnetic signatures of nerves, muscles, fluid and other organs can result in a comprehensive four-dimensional image of structure and function.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention.

Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed is:

1. A system comprising:
    (a) a plurality of non-resistive contact electric field sensors positioned at an entity, each of the plurality of non-resistive contact electric field sensors being positioned proximate a different particular generally predetermined location;
    (b) one or more non-transitory computer readable media containing computer executable instructions executable by a computer processor for
        (i) repeatedly measuring, utilizing the plurality of non-resistive contact electric field sensors, an electrical potential associated with two or more sections of an electrically active structure of the entity;
        (ii) accessing, from a database, data corresponding to past measurements of the electrically active structure taken utilizing non-resistive contact electric field sensors;
        (iii) electronically determining, by comparing data obtained from the repeated measuring to the accessed data, a current property of the electrically active structure of the entity; and
        (iv) generating, utilizing data obtained from the repeated measuring, a visualization of the electrically active structure of the entity of which the current property is determined, the visualization including a depiction of each of the two or more sections of the electrically active structure, together with a visualization of a typical state of the electrically active structure generated based on the accessed data.

2. The system of claim 1, wherein the one or more computer readable media contain computer executable instructions for generating a visualization which utilizes fixed shapes.

3. The system of claim 1, wherein the or more computer readable media contain computer executable instructions for generating a visualization which utilizes variable shapes.

4. The system of claim 1, wherein the one or more computer readable media contain computer executable instructions for generating a visualization which utilizes colors.

5. The system of claim 1, wherein the one or more computer readable media contain computer executable instructions for generating a visualization which utilizes two dimensional displays.

6. The system of claim 1, wherein the one or more computer readable media contain computer executable instructions for generating a visualization which utilizes three dimensional displays.

7. The system of claim 1, wherein the one or more computer readable media contain computer executable instructions for generating a visualization which utilizes sound.

8. The system of claim 1, wherein the one or more computer readable media contain computer executable instructions for generating a visualization which is static.

9. The system of claim 1, wherein the one or more computer readable media contain computer executable instructions for generating a visualization which is dynamic.

10. The system of claim 1, wherein the one or more computer readable media contain computer executable instructions for generating a visualization which utilizes texture.

11. The system of claim 1, wherein the one or more computer readable media contain computer executable instructions for generating a visualization which utilizes heat.

12. The system of claim 1, wherein the one or more computer readable media contain computer executable instructions for generating a visualization which utilizes holograms.

13. The system of claim 1, wherein the one or more computer readable media contain computer executable instructions for generating a visualization which comprises video.

14. The system of claim 1, wherein the system includes one or more additional sensors comprising a sonar sensor.

15. The system of claim 1, wherein the system includes one or more additional sensors comprising an electrometer.

16. The system of claim 1, wherein the system includes one or more additional sensors comprising a magnetometer.

17. The system of claim 1, wherein the system includes one or more additional sensors comprising a camera.

18. The system of claim 1, wherein the system includes one or more additional sensors comprising a thermometer.

19. The system of claim 1, wherein the system includes one or more additional sensors comprising a hydrometer.

20. The system of claim 1, wherein the system includes one or more additional sensors comprising a resistive contact electrometer.

* * * * *